(12) United States Patent
Sugiyama et al.

(10) Patent No.: US 8,753,262 B2
(45) Date of Patent: Jun. 17, 2014

(54) INTERNAL TREATMENT APPARATUS HAVING CIRCUMFERENTIAL SIDE HOLES

(75) Inventors: Akira Sugiyama, Kanagawa (JP); Kenichi Ohara, Gunma (JP); Hiroshi Sano, Chiba (JP); Kunitoshi Ikeda, Tokyo (JP); Tadao Kakizoe, Tokyo (JP); Toshiaki Kobayashi, Tokyo (JP)

(73) Assignees: Hoya Corporation, Tokyo (JP); National Cancer Center, Tokyo (JP)

( * ) Notice: Subject to any disclaimer, the term of this patent is extended or adjusted under 35 U.S.C. 154(b) by 1582 days.

(21) Appl. No.: 10/566,204

(22) PCT Filed: Jul. 16, 2004

(86) PCT No.: PCT/JP2004/010539
§ 371 (c)(1),
(2), (4) Date: Jan. 27, 2006

(87) PCT Pub. No.: WO2005/009227
PCT Pub. Date: Feb. 3, 2005

(65) Prior Publication Data
US 2008/0051629 A1     Feb. 28, 2008

(30) Foreign Application Priority Data

Jul. 29, 2003 (JP) .................................. 2003-281850
Jan. 20, 2004 (JP) .................................. 2004-11954

(51) Int. Cl.
*A61B 1/00* (2006.01)
*A61B 1/04* (2006.01)

(52) U.S. Cl.
USPC ........................... 600/114; 600/104; 600/153

(58) Field of Classification Search
USPC ................ 600/104, 106, 153, 177–183, 201, 600/203–205, 107, 146, 170, 113–115, 600/121–123, 127–129, 139; 604/102.01–102.03, 264
See application file for complete search history.

(56) References Cited

U.S. PATENT DOCUMENTS 3,835,841 A * 9/1974 Terada ........................... 600/157
4,616,631 A * 10/1986 Takahashi ..................... 600/139
4,807,593 A * 2/1989 Ito .................................. 600/114
5,183,471 A * 2/1993 Wilk .............................. 604/284

(Continued)

FOREIGN PATENT DOCUMENTS

JP    4-144533    5/1992
JP    8-106052    4/1996

(Continued)

OTHER PUBLICATIONS

English Language Abstract of JP 2001-299684.

(Continued)

*Primary Examiner* — Alireza Nia
(74) *Attorney, Agent, or Firm* — Greenblum & Bernstein P.L.C.

(57) ABSTRACT

An internal treatment apparatus for a patient having a flexible tubular body to be introduced into a patient includes a center opening for inserting therethrough an endoscope for observing a target site, the center opening being circular in cross section and disposed at a center of an end face of the flexible tubular body; and a plurality of circumferential apertures through which surgical instruments are inserted for performing a surgical procedure on the target site, the plurality of circumferential apertures being provided in the flexible tubular body at equi-angular intervals around the center opening.

4 Claims, 19 Drawing Sheets

(56) References Cited

U.S. PATENT DOCUMENTS

| | | | |
|---|---|---|---|
| 5,354,279 A * | 10/1994 | Hofling | 604/164.12 |
| 5,464,395 A * | 11/1995 | Faxon et al. | 604/103.02 |
| 5,499,630 A * | 3/1996 | Hiki et al. | 600/461 |
| 5,716,321 A * | 2/1998 | Kerin et al. | 600/114 |
| 5,813,976 A * | 9/1998 | Filipi et al. | 600/102 |
| 5,984,932 A * | 11/1999 | Yoon | 606/147 |
| 6,013,024 A * | 1/2000 | Mitsuda et al. | 600/146 |
| 6,302,875 B1 * | 10/2001 | Makower et al. | 604/528 |
| 6,352,503 B1 * | 3/2002 | Matsui et al. | 600/104 |
| 6,440,061 B1 * | 8/2002 | Wenner et al. | 600/114 |
| 6,458,076 B1 * | 10/2002 | Pruitt | 600/146 |
| 6,602,251 B2 | 8/2003 | Burbank et al. | |
| 6,761,685 B2 * | 7/2004 | Adams et al. | 600/121 |
| 6,873,868 B2 * | 3/2005 | Furnish | 600/435 |
| 6,908,427 B2 * | 6/2005 | Fleener et al. | 600/104 |
| 7,029,435 B2 * | 4/2006 | Nakao | 600/153 |
| 7,316,655 B2 * | 1/2008 | Garibotto et al. | 600/585 |
| 7,591,781 B2 * | 9/2009 | Hirata | 600/114 |
| 7,637,905 B2 * | 12/2009 | Saadat et al. | 606/1 |
| 7,846,172 B2 * | 12/2010 | Makower | 606/159 |
| 2001/0014805 A1 | 8/2001 | Burbank et al. | |
| 2001/0049509 A1 * | 12/2001 | Sekine et al. | 600/104 |
| 2003/0100837 A1 * | 5/2003 | Lys et al. | 600/476 |
| 2004/0138525 A1 * | 7/2004 | Saadat et al. | 600/104 |
| 2006/0009740 A1 * | 1/2006 | Higgins et al. | 604/264 |
| 2006/0178560 A1 * | 8/2006 | Saadat et al. | 600/114 |
| 2006/0241347 A1 * | 10/2006 | Whitehead | 600/146 |
| 2007/0282166 A1 * | 12/2007 | Ayala et al. | 600/123 |
| 2009/0253961 A1 * | 10/2009 | Le et al. | 600/121 |
| 2009/0312645 A1 * | 12/2009 | Weitzner et al. | 600/106 |

FOREIGN PATENT DOCUMENTS

| | | |
|---|---|---|
| JP | 8-322787 | 12/1996 |
| JP | 9-19403 | 1/1997 |
| JP | 9-019403 A | 1/1997 |
| JP | 9-108179 | 4/1997 |
| JP | 2000-37348 | 2/2000 |
| JP | 2000-37390 | 2/2000 |
| JP | 2000-166936 A | 6/2000 |
| JP | 2000-262462 A | 9/2000 |
| JP | 2001-104333 | 4/2001 |
| JP | 2001-277177 | 10/2001 |
| JP | 2001-299684 | 10/2001 |
| JP | 2001-299684 A | 10/2001 |
| JP | 2001-299940 | 10/2001 |
| JP | 2002-531204 | 9/2002 |
| JP | 2004-041580 | 2/2004 |

OTHER PUBLICATIONS

English Language Abstract of JP9-19403.
English Language Abstract of JP2001-277177.
English Language Abstract of JP9-108179.
English Language Abstract of JP2001-299940.
English Language Abstract of JP 2004-041580.
English Language Abstract of JP 2000-37390, Feb. 8, 2000.
English language Abstract of JP 4-144533, May 19, 1992.
English language Abstract of JP 2002-531204, Sep. 24, 2002.
English language Abstract of JP 2000-37348, Feb. 8, 2000.
English language Abstract of JP 8-322787, Dec. 10, 1996.
English language Abstract of JP 2001-299684 A (Oct. 30, 2001).
English language Abstract of JP 9-019403 A (Jan. 21, 1997).
English language Abstract of JP 2000-166936 A (Jun. 20, 2000).
English language Abstract of JP 2000-262462 A (Sep. 26, 2000).

* cited by examiner

INTERNAL TREATMENT APPARATUS HAVING CIRCUMFERENTIAL SIDE HOLES

BACKGROUND OF THE INVENTION

The present invention relates to an internal treatment apparatus for a patient and an internal treatment system for a patient which are designed for severing, or the like, a target site inside a patient (subject), and more particularly, to an apparatus and a system for performing medical treatment on a site of lesion inside a patient.

DESCRIPTION OF THE RELATED ART

In a conventional surgical procedure performed on a site of lesion inside a patient, operators would directly manipulate a surgical instrument that had been introduced into the patient through an incised portion. On the other hand, recent years have also seen a newly developed method for the operator to remotely manipulate a surgical instrument introduced into a patient through an incised portion without directly touching the surgical instrument (For example, see Japanese Patent Laid-Open Publication No. 2001-104333).

The aforementioned surgical procedure performed on a site of lesion inside a patient often requires a plurality of surgical instruments to be introduced through an incised portion at the same time, and in such a case, the length of the incised portion has to be increased in accordance with an increase in the number of surgical instruments to be introduced at the same time.

To perform a surgical procedure on a site of lesion located deep inside a patient away from the body surface, it is also necessary to increase the length of an incised portion because an insufficient length of the incised portion makes it difficult to ensure a sufficient field of view.

Furthermore, during the aforementioned surgical procedure performed on a site of lesion inside a patient, the surgical instrument may obstruct the view window provided by an endoscope to restrict the field of view, thereby possibly making it difficult to view the site of lesion and the surrounding area thereof.

Furthermore, a plurality of surgical instruments being introduced into a patient would readily interfere with each other or with the endoscope, whereby the surgical instruments and the endoscope could not access the site of lesion in some cases.

SUMMARY OF THE INVENTION

According to an aspect of the present invention, an internal treatment apparatus for a patient having a flexible tubular body to be introduced into a patient is provided, the flexible tubular body including a center opening for inserting therethrough an endoscope for observing a target site, the center opening being circular in cross section and disposed at a center of an end face of the flexible tubular body; and a plurality of circumferential apertures through which surgical instruments are inserted for performing a surgical procedure on the target site, the plurality of circumferential apertures being provided in the flexible tubular body at equi-angular intervals around the center opening.

In another embodiment, an internal treatment system for a patient including a flexible tubular body, to be introduced into a patient, the flexible tubular body including a center opening for inserting therethrough an endoscope for observing a target site, the center opening being circular in cross section and disposed at a center of an end face of the flexible tubular body, and a plurality of circumferential apertures through which surgical instruments are inserted for performing a surgical procedure on the target site, the plurality of circumferential apertures being provided in the flexible tubular body at equi-angular intervals around the center opening; a body manipulating device for manipulating the flexible tubular body from outside the patient; an endoscope manipulating device for manipulating the endoscope from outside the patient; and a surgical instrument manipulating device for manipulating the surgical instruments from outside the patient.

In another embodiment, an internal treatment apparatus for a patient including a flexible tubular body to be introduced into a patient, the flexible tubular body including a center opening for inserting therethrough an endoscope for observing a target site, the center opening extending through the flexible tubular body from a center of a distal end face of the flexible tubular body, the distal end face facing the target site, and a plurality of circumferential apertures through which surgical instruments are inserted for performing a surgical procedure on the target site, the plurality of circumferential apertures being provided to extend through the flexible tubular body from a side face of the flexible tubular body.

In another embodiment, an internal treatment system for a patient including a flexible tubular body to be introduced into a patient, the flexible tubular body including a center opening for inserting therethrough an endoscope for observing a target site, the center opening being circular in cross section and extending through the flexible tubular body from a center of a distal end face of the flexible tubular body, the distal end face facing the target site, and a plurality of circumferential apertures through which surgical instruments are inserted for performing a surgical procedure on the target site, the plurality of circumferential apertures being provided to extend through the flexible tubular body from a side face of the flexible tubular body; a body manipulating device for manipulating the flexible tubular body from outside the patient; an endoscope manipulating device for manipulating the endoscope from outside the patient; and a surgical instrument manipulating device for manipulating the surgical instruments from outside the patient.

In another embodiment, an internal treatment apparatus for a patient including a flexible tubular body to be introduced into a patient, the flexible tubular body including a center opening for inserting therethrough an endoscope for observing a target site, the center opening extending through the flexible tubular body from a center of a distal end face of the flexible tubular body, the distal end face facing the target site, and a plurality of circumferential apertures through which surgical instruments are inserted for performing a surgical procedure on the target site, each of the plurality of circumferential apertures being provided to extend through the flexible tubular body in an area including the distal end face and a side face of the flexible tubular body.

In another embodiment, an internal treatment system for a patient including a flexible tubular body to be introduced into a patient, the flexible tubular body including a center opening for inserting therethrough an endoscope for observing a target site, the center opening being circular in cross section and extending through the flexible tubular body from a center of a distal end face of the flexible tubular body, the distal end face facing the target site, and a plurality of circumferential apertures through which surgical instruments are inserted for performing a surgical procedure on the target site, each of the plurality of circumferential apertures being provided to extend through the flexible tubular body in an area including the distal end face and a side face of the flexible tubular body; a body manipulating device for manipulating the flexible tubular body from outside the patient; an endoscope manipulating device for manipulating the endoscope from outside the patient; and a surgical instrument manipulating device for manipulating the surgical instruments from outside the patient.

It is desirable for the endoscope to be a stereoscopic endoscope allowing an operator to stereoscopically observe the target site.

The surgical instrument can include a monitor device allowing an operator to observe a vicinity of a distal end of the surgical instrument.

The surgical instrument can include an illumination device which allows an operator to illuminate a vicinity of the distal end of the surgical instrument with light.

The surgical instrument can include at least one of an air feed device and a water feed device which allows an operator to clean a distal end of the illumination device.

It is desirable for the internal treatment system to further include an image displaying device for displaying an image formed by the endoscope.

It is desirable for the flexible tubular body to include a resiliently deflectable portion.

It is desirable for the surgical instrument to include a resiliently deflectable portion.

It is desirable for the flexible tubular body to include grooves provided between each adjacent the circumferential apertures.

It is desirable for a projection angle of the surgical instruments from the flexible tubular body to be smaller than a half angle of a field-of-view of the endoscope.

It is desirable for the endoscope to include an illumination device which emits white light, and for the surgical instruments to each include an illumination device which emits colored light.

Each illumination device of the surgical instruments can continuously emit colored light.

Alternatively, each illumination device of the surgical instruments can emit colored light intermittedly.

It is desirable for the endoscope to include an illumination device, and for the surgical instruments to each include an illumination device which emits light having light intensity different from that of light emitted from the illumination device of the endoscope.

It is desirable for the internal treatment system for a patient to include an image displaying device for displaying an image provided by the endoscope.

The present disclosure relates to subject matter contained in Japanese Patent Application Nos. 2003-281850 (filed on Jul. 29, 2003) and 2004-11954 (filed on Jan. 20, 2004) which are expressly incorporated herein by reference in their entirety.

DETAILED DESCRIPTION OF THE PREFERRED EMBODIMENTS

[First Embodiment]

Figure 1:
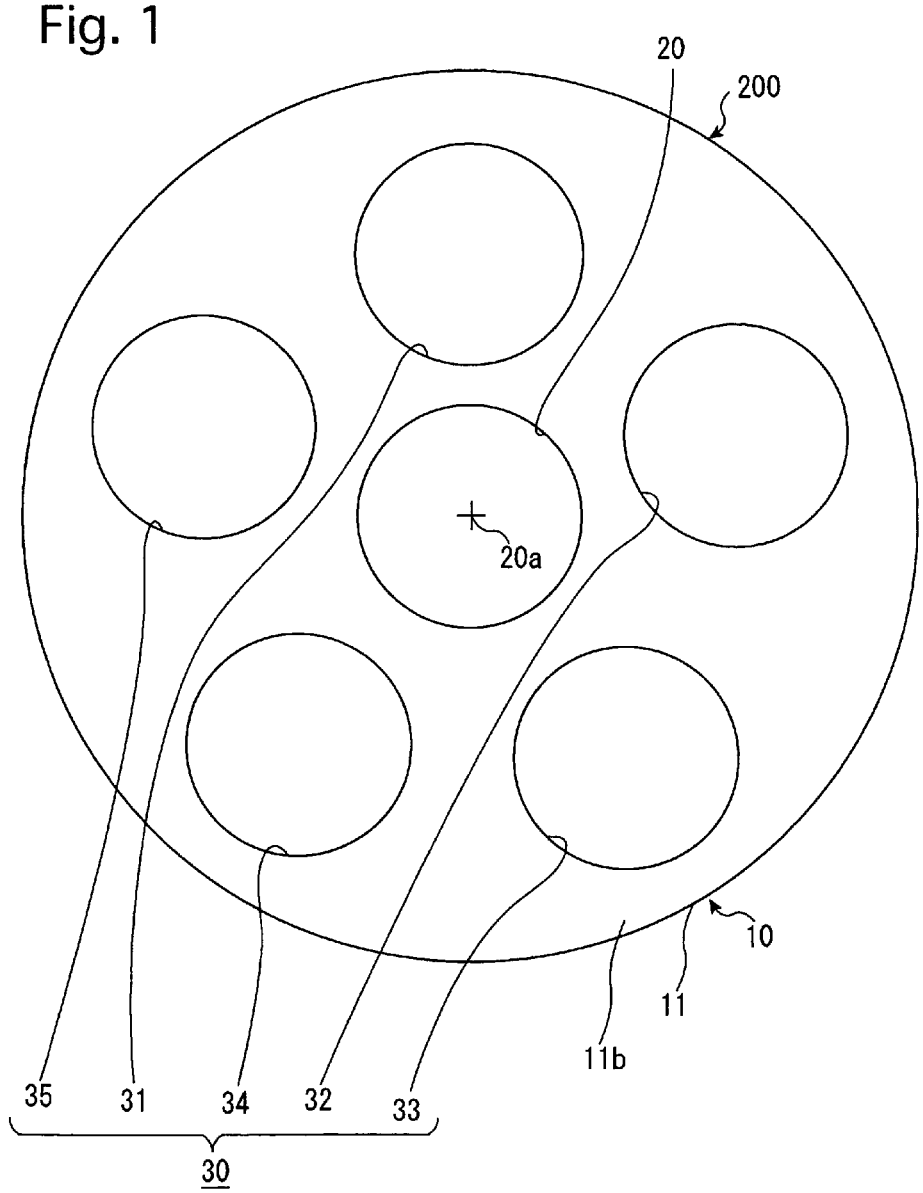
FIG. 1 is a front view showing the configuration of an internal treatment apparatus for a patient according to a first embodiment of the present invention.

A first embodiment of the present invention will be described below in detail with reference to FIGS. 1 to 4. An internal treatment apparatus 200 and an internal treatment system 300 according to this embodiment, which are intended to perform a medical treatment on a site of lesion (target site) inside a patient, include an apparatus body 10 having a center opening 20 and a circumferential opening portion 30. The internal treatment system 300 also includes a body manipulating device 60, endoscope manipulating device 70, and surgical instrument manipulating devices 81 to 85. This embodiment to be described is provided with the circumferential opening portion 30 having five apertures; however, any number of apertures may be included in the circumferential opening portion 30.

Figure 2:
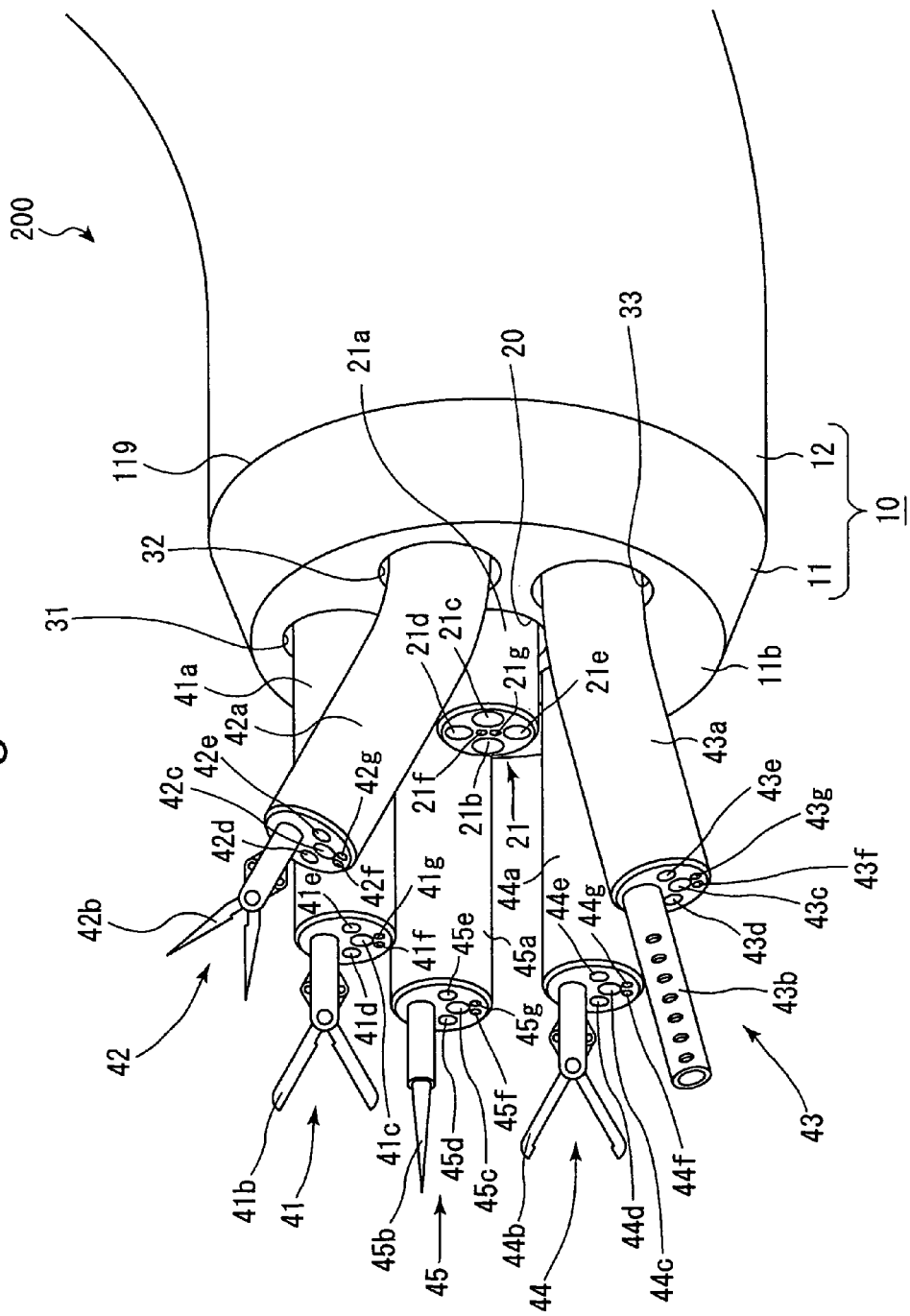
FIG. 2 is a perspective view showing the configuration of the internal treatment apparatus for a patient with surgical instruments and an endoscope being inserted therein in the first embodiment.

For example, the apparatus body 10, which is a flexible tubular member to be introduced into a patient (subject), may have an outer diameter of 5 cm. As shown in FIG. 2, the apparatus body 10 has a distal end portion 11 having a circular cross section with its outer diameter reduced toward the distal end thereof, and a resiliently deflectable portion 12 secured to a rear end face 11a of the distal end portion 11. The apparatus body 10 is introduced into a patient from the tip of the distal end portion 11 so as to access deep inside the patient according to the location of a site of lesion. The apparatus body 10 allows the body manipulating device 60 connected to its proximal end portion to introduce or withdraw the apparatus body 10 into or from the patient and adjust the degree of deflection of the deflectable portion 12. For example, the body manipulating device 60 includes a manual device for the operator to manipulate manually, an automatic feed device, and a winding device, which allow the body manipulating device 60 to make the apparatus body 10 operable from outside the patient.

The apparatus body 10 is provided with the center opening 20, circular in cross section and extending through the center of the cross section thereof, through which an endoscope is inserted for a site of lesion (target site) to be observed. The apparatus body 10 is also provided with the circumferential opening portion 30 of five apertures 31, 32, 33, 34, and 35, which are arranged at equal angular intervals (angular intervals of 72 degrees) about a center 20a of the center opening 20 and extend through the apparatus body 10, so that surgical instruments can be fed therethrough in order for surgical procedures to be performed on the site of lesion. For example, with the apparatus body 10 having an outer diameter of 5 cm, the apertures 31, 32, 33, 34, and 35 each can have an inner diameter of 1.2 cm. The distal end portion 11 and the center opening 20 may not necessarily be circular in cross section. In this case, the five apertures 31, 32, 33, 34, and 35 may be preferably arranged to surround the center opening 20 at equi-angular intervals between adjacent apertures. The center opening 20 and the circumferential opening portion 30 may penetrate through only the distal end portion 11 with the deflectable portion 12 made hollow.

A stereoscopic endoscope 21 is retractably inserted into and extends through the center opening 20. The stereoscopic endoscope 21 has the following components fixedly inserted into a resiliently deflectable cylindrical body 21a: two monitor optical systems 21b and 21c for stereoscopically observing a site of lesion, illumination optical systems 21d and 21e for illuminating the site of lesion with light, an air feed line 21f for feeding air into the patient, and a water feed line 21g for feeding water to the monitor optical systems 21b and 21c to defog or clean the surface thereof. The stereoscopic endoscope 21 is employed in this manner to observe a site of lesion and the surrounding area thereof stereoscopically, thereby making it possible to perform medical treatment precisely and smoothly. Furthermore, the stereoscopic endoscope 21 is connected at the proximal end portion thereof to the endoscope manipulating device 70 for introducing and withdrawing the body 21a; adjusting the focus, field of view, and zooming of the monitor optical systems 21b and 21c; adjusting the brightness, direction, and angle of the illumination optical systems 21d and 21e; feeding water to the monitor optical systems 21b and 21c to defog or clean the surface thereof; and feeding air into the patient. The endoscope manipulating device 70 allows the stereoscopic endoscope 21 to be operable from outside the patient. The monitor optical systems 21b and 21c are connected at the proximal end portion of the stereoscopic endoscope 21 to image displaying device 87 which is capable of displaying stereoscopically the images of the site of lesion and its surrounding provided thereby. It is also acceptable to employ only a single monitor optical system depending on the contents of medical treatment.

Flexible elongated surgical instruments 41, 42, 43, 44, and 45 are retractably inserted into and extend out of the apertures 31, 32, 33, 34, and 35, respectively. The surgical instruments 41, 42, 43, 44, and 45, which each have a resiliently deflectable portion, are connected at their respective proximal end portions to the surgical instrument manipulating devices 81, 82, 83, 84, and 85 to manipulate the surgical instruments. The surgical instruments 41, 42, 43, 44, and 45 may be inserted into any of the apertures 31, 32, 33, 34, and 35 depending on the order of medical treatment steps or the shape of a site of lesion. Any surgical instruments other than the surgical instruments 41, 42, 43, 44, and 45 can also be inserted into the apertures 31, 32, 33, 34, and 35. For example, assuming that the apertures 31, 32, 33, 34, and 35 each have an inner diameter of 1.2 cm, each of the surgical instruments 41, 42, 43, 44, and 45 can have an outer diameter of 1 cm.

For example., the surgical instrument 41 has the following components fixedly inserted into a resiliently deflectable cylindrical body 41a to grasp the surrounding of the site of lesion for excision with the surgical instrument 42 or 45: a grasper forceps 41b capable of grasping an object; a monitor optical system (monitor device) 41c for observing the vicinity of the tips of the grasper forceps 41b; illumination optical systems (illumination device) 41d and 41e for illuminating the vicinity of the tips of the grasper forceps 41b with light; an air feed line 41f (air feed device) for feeding air into the patient; and a water feed line 41g (water feed device) for feeding water to the monitor optical system 41c to defog or clean the surface thereof. The surgical instrument 41 is connected at the proximal end portion thereof to the surgical instrument manipulating device 81 for introducing, withdrawing, and deflecting the body 41a; controlling the grasping operation of the grasper forceps 41b; adjusting the focus, field of view, and zooming of the monitor optical system 41c; adjusting the brightness, direction, and angle of the illumination optical systems 41d and 41e; and feeding water to the monitor optical system 41c to defog or clean the surface thereof and feeding air into the patient. The surgical instrument manipulating device 81 allows the surgical instrument 41 to be operable from outside the patient. The monitor optical system 41c is connected at the proximal end portion of the surgical instrument 41 to image displaying device 91 which is capable of displaying the image of the vicinity of the tips of the grasper forceps 41b provided by the monitor optical system 41c. Two monitor optical systems may also be employed to stereoscopically observe the vicinity of the tips of the grasper forceps 41b. It is also possible to make infrared light observations, fluorescent light observations, zoomed observations, ultrasonic observations, confocal observations, or optical coherent tomographic (OCT) observations.

For example, the surgical instrument 42 has the following components fixedly inserted into a resiliently deflectable cylindrical body 42a to sever the site of lesion whose surrounding is grasped with the surgical instrument 41: a cutting forceps 42b capable of severing an object; a monitor optical system (monitor device) 42c for observing the vicinity of the tips of the cutting forceps 42b; illumination optical systems (illumination device) 42d and 42e for illuminating the vicinity of the tips of the cutting forceps 42b with light; an air feed line 42f (air feed device) for feeding air into the patient; and a water feed line 42g (water feed device) for feeding water to the monitor optical system 42c to defog or clean the surface thereof. The surgical instrument 42 is connected at its proximal end portion to the surgical instrument manipulating device 82 for introducing, withdrawing, and deflecting the body 42a; controlling the severing operation of the cutting forceps 42b; adjusting the focus, field of view, and zooming of the monitor optical system 42c; adjusting the brightness, direction, and angle of the illumination optical systems 42d and 42e; and feeding water to the monitor optical system 42c to defog or clean the surface thereof and feeding air into the patient. The surgical instrument manipulating device 82 makes the surgical instrument 42 operable from outside the patient. The monitor optical system 42c is connected at the proximal end portion of the surgical instrument 42 to image displaying device 92 which is capable of displaying the image of the vicinity of the tips of the cutting forceps 42b provided by the monitor optical system 42c. Two monitor optical systems may also be employed to stereoscopically observe the vicinity of the tips of the cutting forceps 42b. It is also possible to make infrared light observations, fluorescent light observations, zoomed observations, ultrasonic observations, confocal observations, or optical coherent tomographic observations (OCT).

The surgical instrument 43 has the following components fixedly inserted into a resiliently deflectable cylindrical body 43a to feed water for cleaning the site of lesion and the surrounding area thereof and apply suction to a liquid such as blood or cleaning water at the site of lesion and the surrounding area thereof. The components include a cleaning water feed/suction tube 43b for feeding water to clean the site of lesion and the surrounding area thereof and applying suction to a liquid such as blood or cleaning water at the site of lesion and the surrounding area thereof from outside the patient; a monitor optical system (monitor device) 43c for observing the vicinity of the tip of the cleaning water feed/suction tube 43b; illumination optical systems (illumination device) 43d and 43e for illuminating the vicinity of the tip of the cleaning water feed/suction tube 43b with light; and an air feed line 43f (air feed device) for feeding air into the patient and a water feed line 43g (water feed device) for feeding water to the monitor optical system 43c to defog or clean the surface thereof. The surgical instrument 43 is connected at its proximal end portion to the surgical instrument manipulating device 83 for introducing, withdrawing, and deflecting the body 43a; controlling the feeding of water and applications of suction by the cleaning water feed/suction tube 43b; adjusting the focus, field of view, and zooming of the monitor optical system 43c; adjusting the brightness, direction, and angle of the illumination optical systems 43d and 43e; and feeding water to the monitor optical system 43c to defog or clean the surface thereof and feeding air into the patient. The surgical instrument manipulating device 83 makes the surgical instrument 43 operable from outside the patient. The monitor optical system 43c is connected at the proximal end portion of the surgical instrument 43 to image displaying device 93 which is capable of displaying the image of the vicinity of the tip of the cleaning water feed/suction tube 43b provided by the monitor optical system 43c. Two monitor optical systems may also be employed to stereoscopically observe the vicinity of the tip of the cleaning water feed/suction tube 43b. It is also possible to make infrared light observations, fluorescent light observations, zoomed observations, ultrasonic observations, confocal observations, or optical coherent tomographic (OCT) observations.

The surgical instrument 44 has the following components fixedly inserted into a resiliently deflectable cylindrical body 44a to locally stop bleeding at a desired portion: an RF hemostatic forceps 44b for applying a radio frequency to a desired portion and thereby generating heat to stop bleeding; a monitor optical system (monitor device) 44c for observing the vicinity of the tips of the RF hemostatic forceps 44b; illumination optical systems (illumination devices) 44d and 44e for illuminating the vicinity of the tips of the RF hemostatic forceps 44b with light; an air feed line 44f (air feed device) for feeding air into the patient; and a water feed line 44g (water feed device) for feeding water to the monitor optical system 44c to defog or clean the surface thereof. The surgical instrument 44 is connected at the proximal end portion thereof to the surgical instrument manipulating device 84 for introducing, withdrawing, and deflecting the body 44a; controlling the hemostatic operations provided by the RF hemostatic forceps 44b; adjusting the focus, field of view, and zooming of the monitor optical system 44c; adjusting the brightness, direction, and angle of the illumination optical systems 44d and 44e; and feeding water to the monitor optical system 44c to defog or clean the surface thereof and feeding air into the patient. The surgical instrument manipulating device 84 allows the surgical instrument 44 to be operable from outside the patient. The monitor optical system 44c is connected at the proximal end portion of the surgical instrument 44 to an image displaying device 94 which is capable of displaying the image of the vicinity of the tips of the RF hemostatic forceps 44b provided by the monitor optical system 44c. Two monitor optical systems may also be employed to stereoscopically observe the vicinity of the tips of the RF hemostatic forceps 44b. It is also possible to make infrared light observations, fluorescent light observations, zoomed observations, ultrasonic observations, confocal observations, or optical coherent tomographic observations (OCT).

The surgical instrument 45 has the following components fixedly inserted into a resiliently deflectable cylindrical body 45a to incise a desired portion: an RF incision knife 45b for pushing its RF-vibrating tip portion against a desired portion for incision; a monitor optical system (monitor device) 45c for observing the vicinity of the tip of the RF incision knife 45b; illumination optical systems (illumination device) 45d and 45e for illuminating the vicinity of the tip of the RF incision knife 45b with light; an air feed line 45f (air feed device) for feeding air into the patient; and a water feed line 45g (water feed device) for feeding water to the monitor optical system 45c to defog or clean the surface thereof. The surgical instrument 45 is connected at the proximal end portion thereof to the surgical instrument manipulating device 85 for introducing, withdrawing, and deflecting the body 45a; controlling the incision operations provided by the RF incision knife 45b; adjusting the focus, field of view, and zooming of the monitor optical system 45c; adjusting the brightness, direction, and angle of the illumination optical systems 45d and 45e; and feeding water to the monitor optical system 45c to defog or clean the surface thereof and feeding air into the patient. The surgical instrument manipulating device 85 allows the surgical instrument 45 to be operable from outside the patient. The monitor optical system 45c is connected at the proximal end portion of the surgical instrument 45 to image displaying device 95 which is capable of displaying the image of the vicinity of the tip of the RF incision knife 45b provided by the monitor optical system 45c. Two monitor optical systems may also be employed to stereoscopically observe the vicinity of the tip of RF incision knife 45b. It is also possible to make infrared light observations, fluorescent light observations, zoomed observations, ultrasonic observations, confocal observations, or optical coherent tomographic observations (OCT).

The following is an explanation on a surgical procedure performed on a site of lesion using the aforementioned internal treatment apparatus 200 and the internal treatment system 300. First, an adequate portion is incised to perform the surgical procedure on a site of lesion in a patient. Even for a surgical procedure that requires a plurality of surgical instruments, the internal treatment apparatus 200 only requires an incised portion just large enough to introduce therethrough the internal treatment apparatus 200 into the patient (e.g., about 5 cm for the apparatus body 10 having an outer diameter of 5 cm), thereby reducing the burden on the patient.

Figure 3:
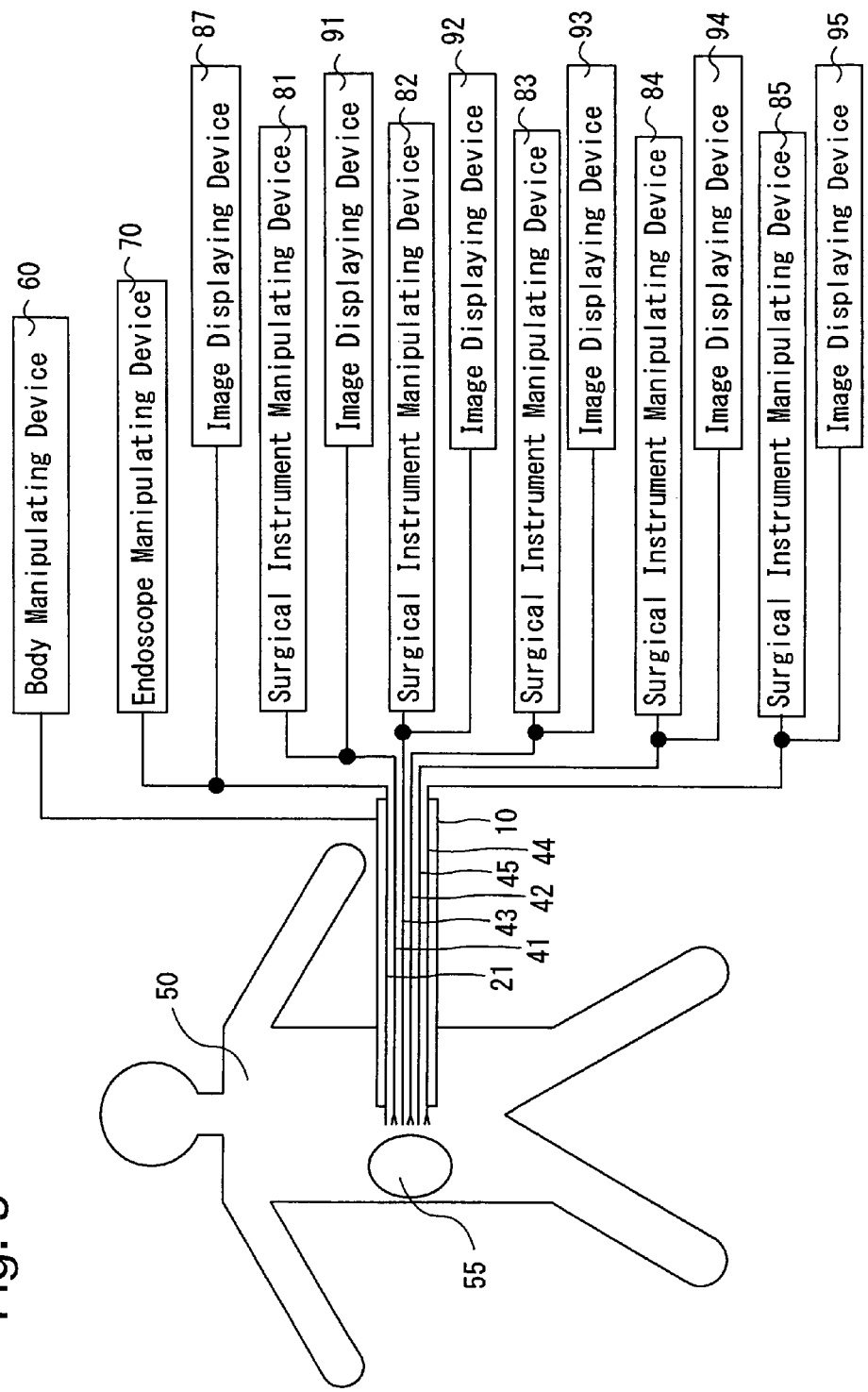
FIG. 3 is a block diagram showing the relation between a body, an endoscope, and surgical instruments, and body manipulating device, endoscope manipulating device, surgical instrument manipulating device, and image displaying device according to the first embodiment of the present invention.
Figure 4:
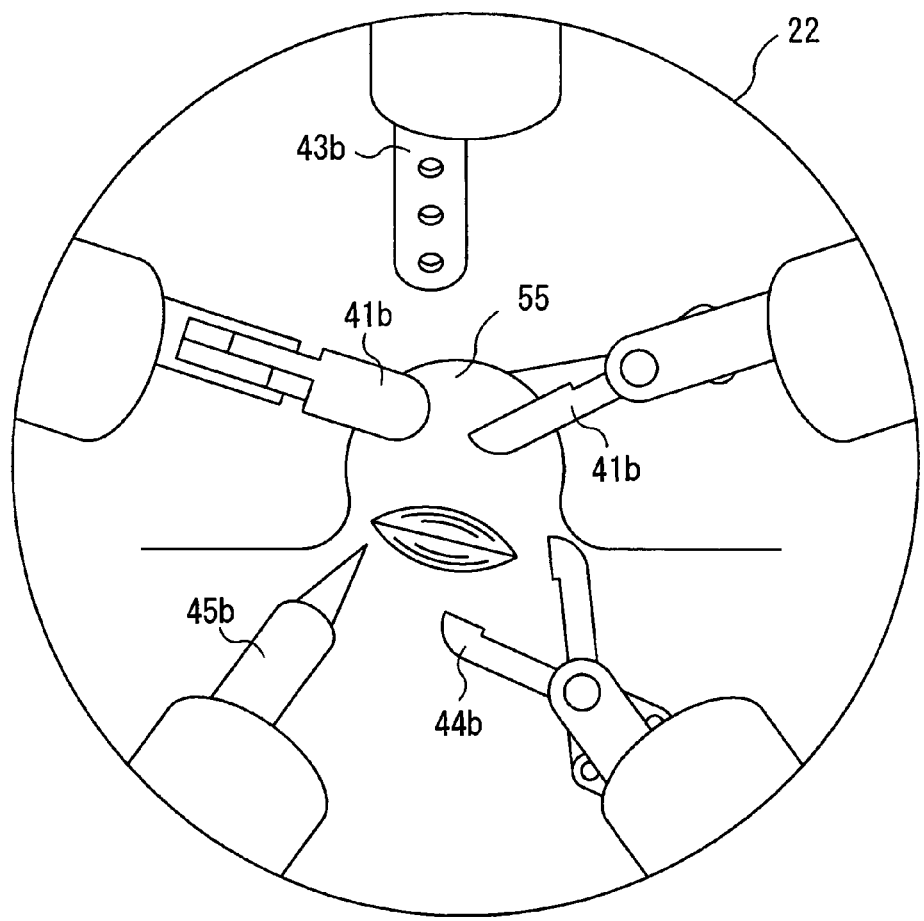
FIG. 4 is a view showing an example of a surgical procedure being performed within a range of view of the endoscope according to the first embodiment of the present invention.

Thereafter, the internal treatment apparatus 200 is introduced into a patient 50 through the incised portion. Before the insertion, the body manipulating device 60 is connected to the apparatus body 10, the endoscope manipulating device 70 and the image displaying device 87 are connected to the stereoscopic endoscope 21, the surgical instrument manipulating devices 81 through 85 are connected to the surgical instruments 41 through 45, respectively, and the image displaying devices 91 through 95 are connected to the surgical instruments 41 through 45, respectively, as shown in FIG. 3. The internal treatment apparatus 200 is introduced into the patient and then stopped, so as to commence the surgical procedure when a view range 22 of the stereoscopic endoscope 21 allows the operator to view a lesion 55 and the surrounding area thereof and each tip portion of the surgical instruments 41, 42, 43, 44, and 45, as shown in FIG. 4.

The internal treatment apparatus 200 is designed such that the surgical instruments 41 through 45 are arranged to surround the stereoscopic endoscope 21, thereby allowing the surgical instruments 41 through 45 to be placed along the entire circumference of a view range provided by the stereoscopic endoscope 21 during the surgical procedure. This allows the operator to easily recognize the lesion 55 and the surgical instruments 41 through 45, thereby facilitating the manipulation thereof. Additionally, the surgical instruments can be replaced as appropriate to facilitate a surgical operation. For example, as shown in FIG. 4, two grasper forceps 41*b* can be used to elevate the lesion 55 at the left and right sides thereof. The RF incision knife 45*b* is then used to sever the lesion 55 at a base thereof, and the RF hemostatic forceps 44*b* and the cleaning water feed/suction tube 43*b* are then used to stop bleeding and feed cleaning water from above as required. Furthermore, for a lesion 55 located deep inside the patient, the internal treatment apparatus 200 can be introduced deep into the patient to provide a view range as shown in FIG. 4, thereby allowing the surgical procedure to be performed smoothly with safety.

Figure 5:
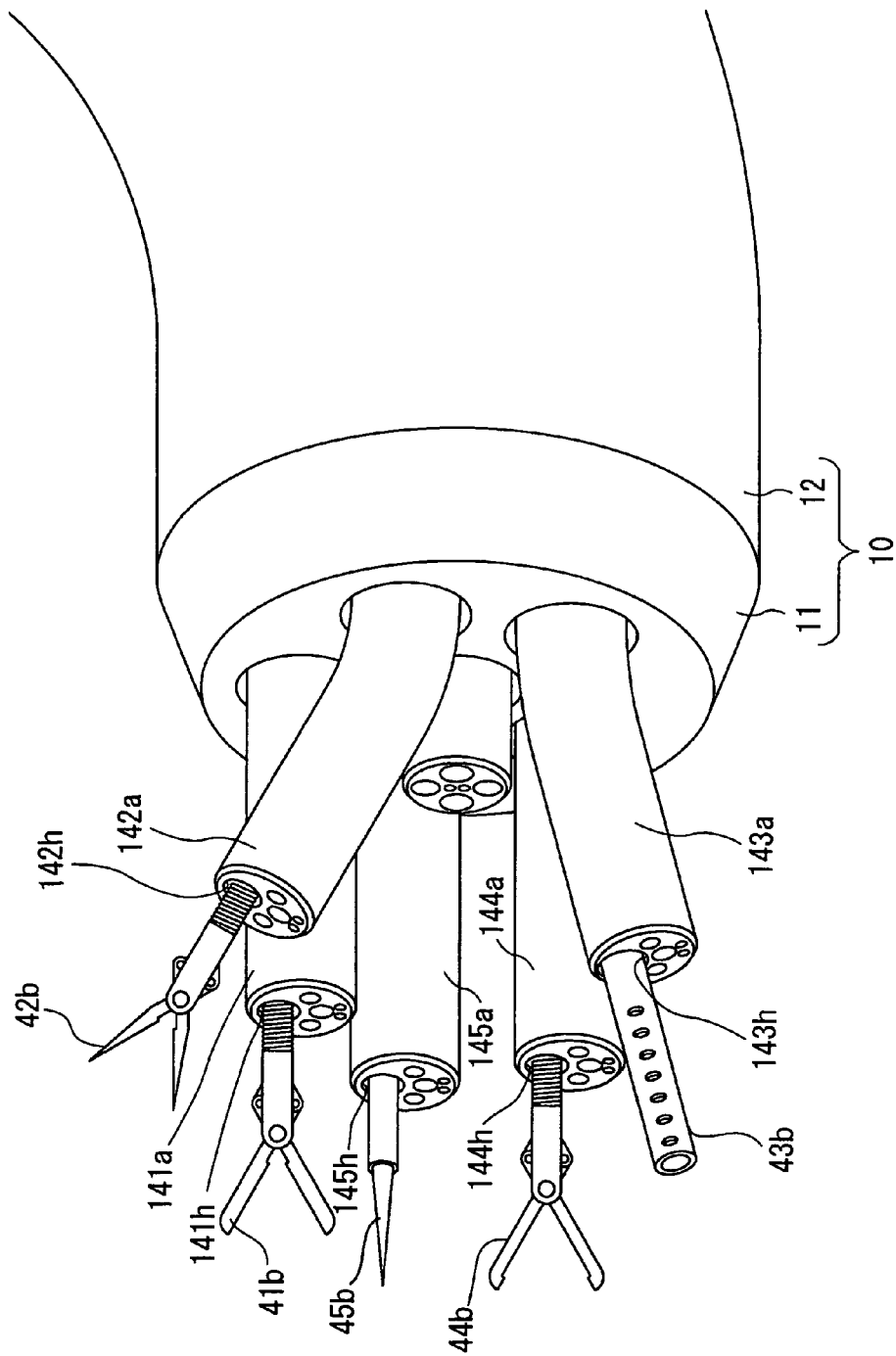
FIG. 5 is a perspective view showing the configuration of a modified example of the first embodiment of the present invention.

A modified example will be explained below. As shown in FIG. 5, the resiliently deflectable cylindrical bodies 41*a*, 42*a*, 43*a*, 44*a*, and 45*a* can be replaced with endoscopic insertion portions 141*a*, 142*a*, 143*a*, 144*a*, and 145*a*, respectively. In this case, the grasper forceps 41*b*, the cutting forceps 42*b*, the cleaning water feed/suction tube 43*b*, the RF hemostatic forceps 44*b*, and the RF incision knife 45*b* are passed through forceps channels 141*h*, 142*h*, 143*h*, 144*h*, and 145*h* which are provided in the endoscopic insertion portions 141*a*, 142*a*, 143*a*, 144*a*, and 145*a*, respectively. Likewise with the surgical instruments 41, 42, 43, 44, and 45, the endoscopic insertion portions 141*a*, 142*a*, 143*a*, 144*a*, and 145*a* are provided with a monitor optical system, an illumination optical system, an air feed line, a water feed line, and a deflectable portion. This configuration allows for utilizing an existing endoscope, thereby reducing manufacturing costs.

Figure 6:
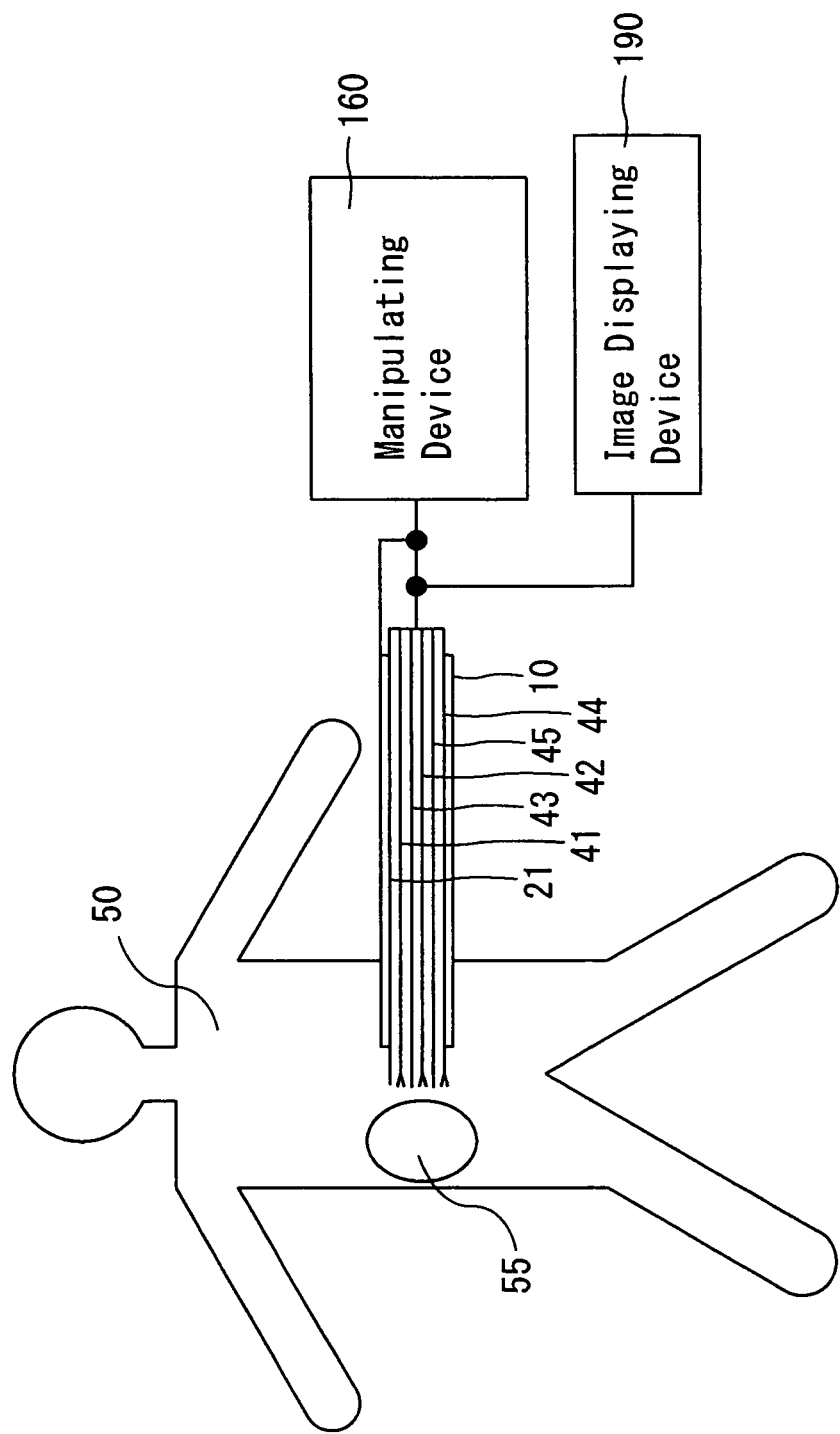
FIG. 6 is a block diagram showing the relation between a body, an endoscope, and surgical instruments, and manipulating device and image displaying device according to the modified example of the first embodiment of the present invention.

As shown in FIG. 6, the body manipulating device 60, the endoscope manipulating device 70, and the surgical instrument manipulating devices 81 through 85 can be replaced with a manipulating device 160 which allows the operator to collectively or selectively manipulate the apparatus body 10, the stereoscopic endoscope 21, and the surgical instruments 41 through 45. The image displaying device 87 and the image displaying device 91 through 95 can be replaced with an image display device 190 which can collectively or selectively display images from the monitor optical systems 21*b* and 21*c* of the stereoscopic endoscope 21 and from the monitor optical systems 41*c*, 42*c*, 43*c*, 44*c*, and 45*c* of the surgical instruments 41 through 45. This configuration provides a space-saving, compact system, allowing a less number of operators to efficiently perform surgical procedures.

[Second Embodiment]

A second embodiment of the present invention will be described below in detail with reference to FIGS. 7 through 14. An internal treatment apparatus 400 and an internal treatment system 500 (FIG. 14) according to the second embodiment, which are intended to perform a medical treatment on a site of lesion (target site) inside a patient, include an apparatus body 10*a* having a center opening 220 and a circumferential opening portion 130. The internal treatment system 500 further includes a body manipulating device 260, a endoscope manipulating device 170, and surgical instrument manipulating devices 181 and 182.

Figure 9:
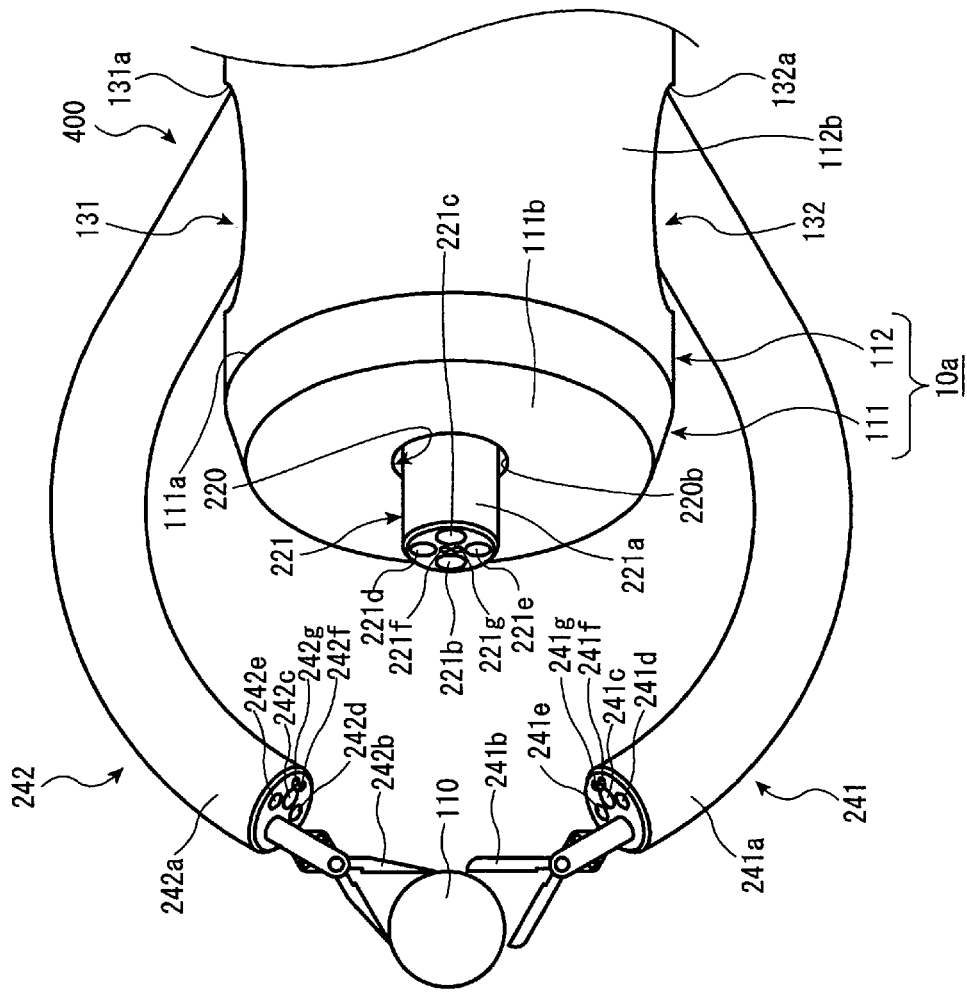
FIG. 9 is a perspective view showing the configuration of the internal treatment apparatus with surgical instruments and an endoscope being inserted therein in the second embodiment.

The apparatus body 10*a* can be formed as a flexible tubular member to be introduced into a patient (subject). As shown in FIG. 9, the apparatus body 10*a* includes a distal end portion 111 having a circular cross section with the outer diameter thereof reduced toward its distal end, and a resiliently deflectable portion 112 secured to a rear end face 111*a* of the distal end portion 111. The apparatus body 10*a* is introduced into a patient from the tip of the distal end portion 111 so as to reach deep inside the patient to the location of a site of lesion. The apparatus body 10*a* allows the body manipulating device 260 (FIG. 14) connected to the proximal end portion thereof to introduce or withdraw the apparatus body 10*a* into or from the patient and adjust the degree of deflection of the deflectable portion 112. For example, the body manipulating device 260 includes a manual device for the operator for manual manipulation, an automatic feed device, and a winding device, which allows the body manipulating device 260 to make the apparatus body 10*a* operable from outside the patient.

The cylindrical apparatus body 10*a* is provided with the circular center opening 220, which passes through the apparatus body 10*a* from the center of one bottom face (distal end face) 111*b* of the two bottom faces, the bottom face 111*b* facing the lesion 55, toward the other bottom face (proximal end face, not shown). The apparatus body 10*a* is further provided with the circumferential opening portion 130 which passes through the apparatus body 10*a* from a side face 112*b* of the deflectable portion 112 toward a proximal end face 10*c* (FIG. 14) of the apparatus body 10*a*. A stereoscopic endoscope 221 for observing a site of lesion (target site) is inserted through the center opening 220 to protrude from an outlet 220*b* to the lesion 55. The circumferential opening portion 130 includes two circular apertures 131 and 132 disposed at equi-angular intervals (at intervals of 180 degrees in this embodiment) about a center 220*a* of the center opening 220. Surgical instruments 242 and 241 for performing a surgical procedure on a site of lesion are passed through the apertures 131 and 132 to protrude outwardly from outlets 131*a* and 132*a*, respectively. The distance between the outlet 131*a* and the distal end face 111*b* is equal to that between the outlet 132*a* and the distal end face 111*b*. The outlets 131*a* and 132*a* being preferably equal in inner diameter would allow the surgical instruments 241 and 242 to be replaced according to the contents and steps of surgical procedures. It is also desirable to make the inner diameter of the outlets 131a and 132a greater than the outer diameter of the surgical instruments 241 and 242 to use the surgical instruments 241 and 242 at desired angles.

The apparatus body 10a having the apertures 131 and 132 can be formed according to an existing technique. For example, it is possible to form the apparatus body 10a having the apertures 131 and 132 by molding a heat meltable resin in a mold having a cylindrical portion the same in shape as the apertures 131 and 132 and then solidifying the resin by cooling. The apertures 131 and 132 formed in this manner would prevent the endoscope and two surgical instruments from being entangled or interfering with each other inside the apparatus body 10a, thereby eliminating the difficulty of manipulating them. For example, the apparatus body 10a formed as described above may have an outer diameter of 5 cm with the apertures 131 and 132 each having an inner diameter of 1.2 cm. On the other hand, the distal end portion 111 and the center opening 220 may have not necessarily to be circular in cross section.

Figure 14:
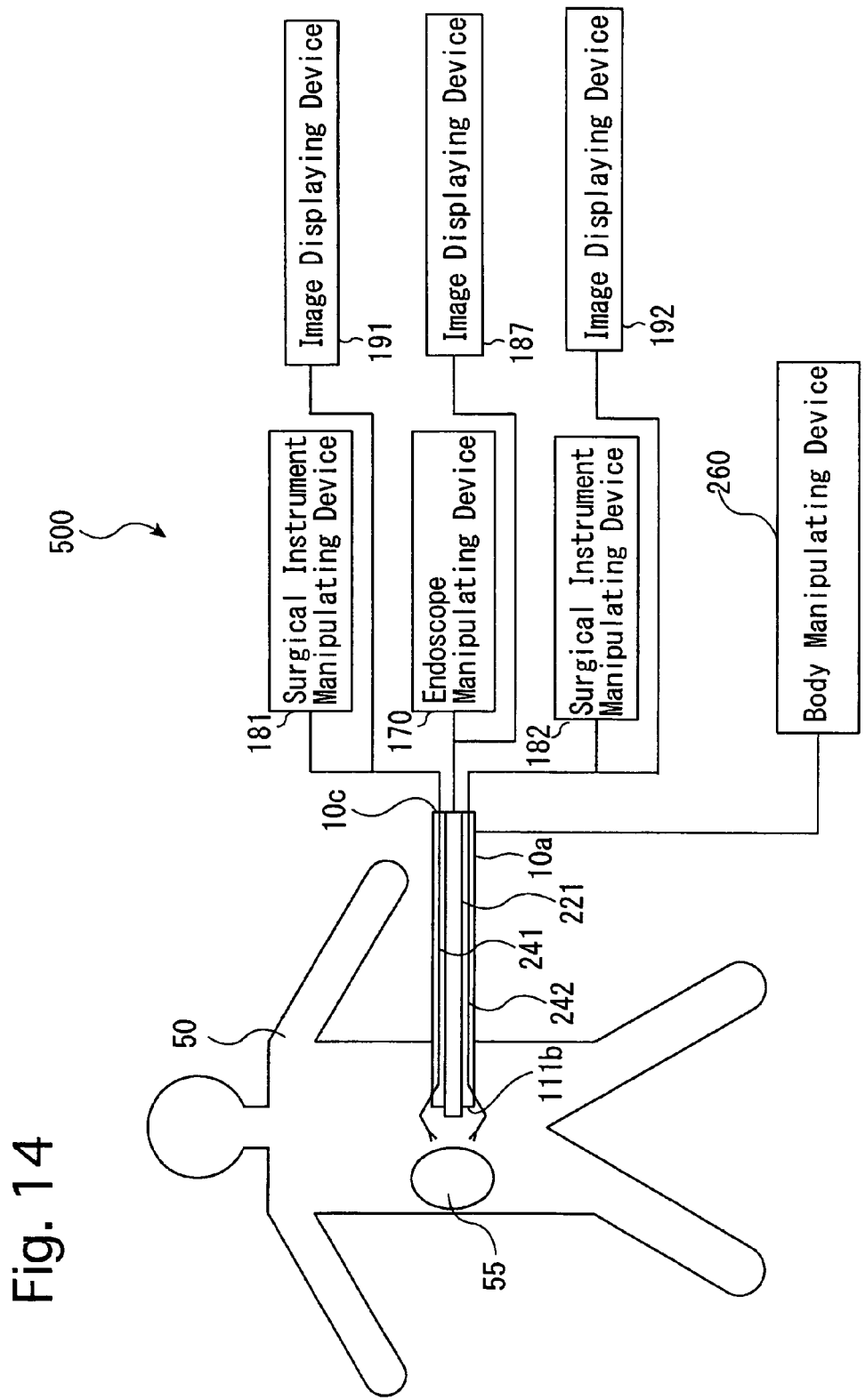
FIG. 14 is a block diagram showing the relation between a body, an endoscope, and surgical instruments, and body manipulating device, endoscope manipulating device, surgical instrument manipulating device, and image displaying device according to the second embodiment of the present invention.

As shown in FIG. 9, the stereoscopic endoscope 221 has the following components fixedly inserted into a resiliently deflectable cylindrical body 221a. The components include two monitor optical systems 221b and 221c for stereoscopically observing a site of lesion; illumination optical systems 221d and 221e for illuminating the site of lesion with light; an air feed line 221f for feeding air into the patient; and a water feed line 221g for feeding water to the monitor optical systems 221b and 221c to defog or clean the surface thereof. The stereoscopic endoscope 221 is employed in this manner to observe a site of lesion and the surrounding area thereof stereoscopically, thereby making it possible to perform medical treatment precisely and smoothly. Furthermore, as shown in FIG. 14, the stereoscopic endoscope 221 is connected at the proximal end portion thereof to the endoscope manipulating device 170 for introducing and withdrawing the body 221a; adjusting the focus, field of view, and zooming of the monitor optical systems 221b and 221c; adjusting the brightness, direction, and angle of the illumination optical systems 221d and 221e; and feeding water to the monitor optical systems 221b and 221c to defog or clean the surface thereof and feeding air into the patient. This allows the endoscope manipulating device 170 to make the stereoscopic endoscope 221 operable from outside the patient. The monitor optical systems 221b and 221c are connected at the proximal end portion of the stereoscopic endoscope 221 to image displaying device 187 which is capable of displaying stereoscopically the images of the site of lesion and its surrounding provided thereby. It is also possible to employ only a single monitor optical system depending on the contents of medical treatments.

For example, as shown in FIG. 9, the surgical instrument 241 has the following components fixedly inserted into a resiliently deflectable cylindrical body 241a to sever the site of lesion whose surrounding is grasped with the surgical instrument 242: a cutting forceps 241b capable of severing an object; a monitor optical system (monitor device) 241c for observing the vicinity of the tips of the cutting forceps 241b; illumination optical systems (illumination device) 241d and 241e for illuminating the vicinity of the tips of the cutting forceps 241b with light; and an air feed line 241f (air feed device) for feeding air into the patient and a water feed line 241g (water feed device) for feeding water to the monitor optical system 241c to defog or clean the surface thereof. As shown in FIG. 14, the surgical instrument 241 is connected at the proximal end portion thereof to the surgical instrument manipulating device 181 for introducing, withdrawing, and deflecting the body 241a; controlling the severing operation of the cutting forceps 241b; adjusting the focus, field of view, and zooming of the monitor optical system 241c; adjusting the brightness, direction, and angle of the illumination optical systems 241d and 241e; and feeding water to the monitor optical system 241c to defog or clean the surface thereof and feeding air into the patient. This allows the surgical instrument manipulating device 181 to make the surgical instrument 241 operable from outside the patient. The monitor optical system 241c is connected at the proximal end portion of the surgical instrument 241 to an image displaying device 191 which is capable of displaying the image of the vicinity of the tips of the cutting forceps 241b provided by the monitor optical system 241c. Two monitor optical systems may also be employed to stereoscopically observe the vicinity of the tips of the cutting forceps 241b. It is also possible to make infrared light observations, fluorescent light observations, zoomed observations, ultrasonic observations, confocal observations, or optical coherent tomographic (OCT) observations.

For example, as shown in FIG. 9, the surgical instrument 242 has the following components fixedly inserted into a resiliently deflectable cylindrical body 242a to sever the site of lesion whose surrounding is grasped with the surgical instrument 241: a cutting forceps 242b capable of severing an object; a monitor optical system (monitor device) 242c for observing the vicinity of the tips of the cutting forceps 242b; illumination optical systems (illumination device) 242d and 242e for illuminating the vicinity of the tips of the cutting forceps 242b with light; and an air feed line 242f (air feed device) for feeding air into the patient and a water feed line 242g (water feed device) for feeding water to the monitor optical system 242c to defog or clean the surface thereof. As shown in FIG. 14, the surgical instrument 242 is connected at its proximal end portion to the surgical instrument manipulating device 182 for introducing, withdrawing, and deflecting the body 242a; controlling the severing operation of the cutting forceps 242b; adjusting the focus, field of view, and zooming of the monitor optical system 242c; adjusting the brightness, direction, and angle of the illumination optical systems 242d and 242e; and feeding water to the monitor optical system 242c to defog or clean the surface thereof and feeding air into the patient. This allows the surgical instrument manipulating device 182 to make the surgical instrument 242 operable from outside the patient. The monitor optical system 242c is connected at the proximal end portion of the surgical instrument 242 to an image displaying device 192 which is capable of displaying the image of the vicinity of the tips of the cutting forceps 242b provided by the monitor optical system 242c. Two monitor optical systems may also be employed to stereoscopically observe the vicinity of the tips of the cutting forceps 242b. It is also possible to make infrared light observations, fluorescent light observations, zoomed observations, ultrasonic observations, confocal observations, or optical coherent tomographic (OCT) observations.

The surgical instruments 241 and 242 may be inserted into any of the apertures 131 and 132 depending on the order of medical treatment steps or the shape of a site of lesion. Any surgical instruments other than the surgical instruments 241 and 242 can also be inserted into the apertures 131 and 132. For example, assuming that the apertures 131 and 132 each have an inner diameter of 1.2 cm, each of the surgical instruments 241 and 242 can have an outer diameter of 1 cm.

Figure 10:
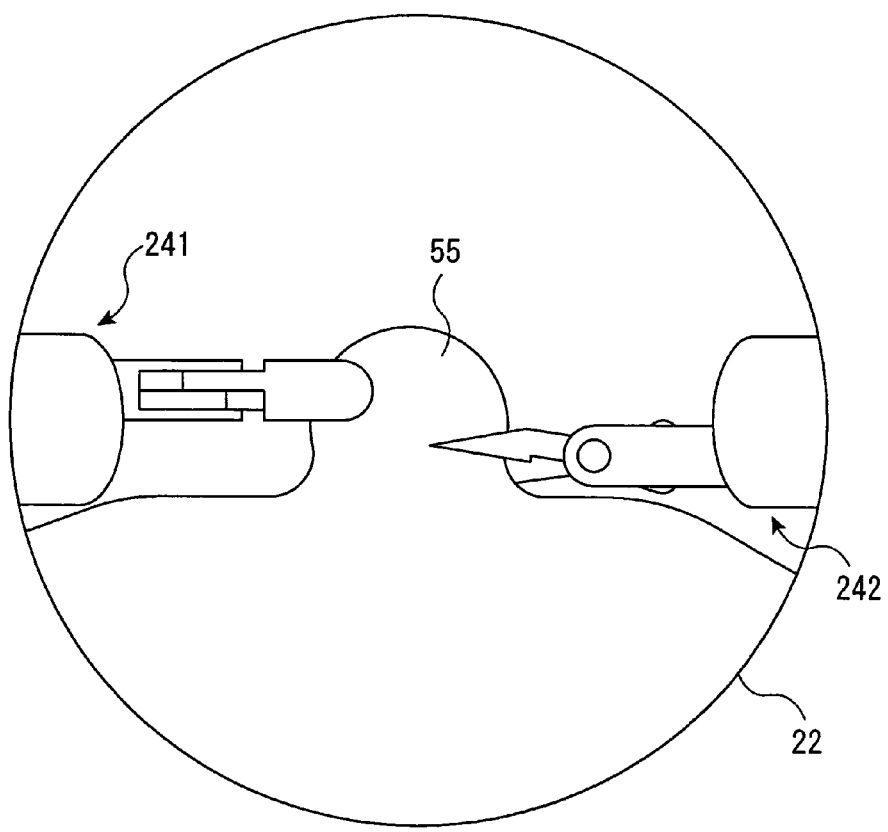
FIG. 10 is a view showing an example of a surgical procedure being performed within a range of view of the endoscope according to the second embodiment of the present invention.

In this manner, the stereoscopic endoscope 221 protrudes from the distal end face 111b while the surgical instruments 241 and 242 are protruded from the side faces, thereby reducing the risk of the surgical instruments 241 and 242 being tangled with each other inside the patient 50. Accordingly, the stereoscopic endoscope 221 and the surgical instruments 241 and 242 can be easily placed at desired positions. Furthermore, as shown in FIG. 10, the surgical instruments 241 and 242 access the lesion 55 from right and left sides within the view range provided by the stereoscopic endoscope 221, thereby allowing the operator to view an enlarged range without being obstructed by the surgical instruments 241 and 242.

Figure 11:
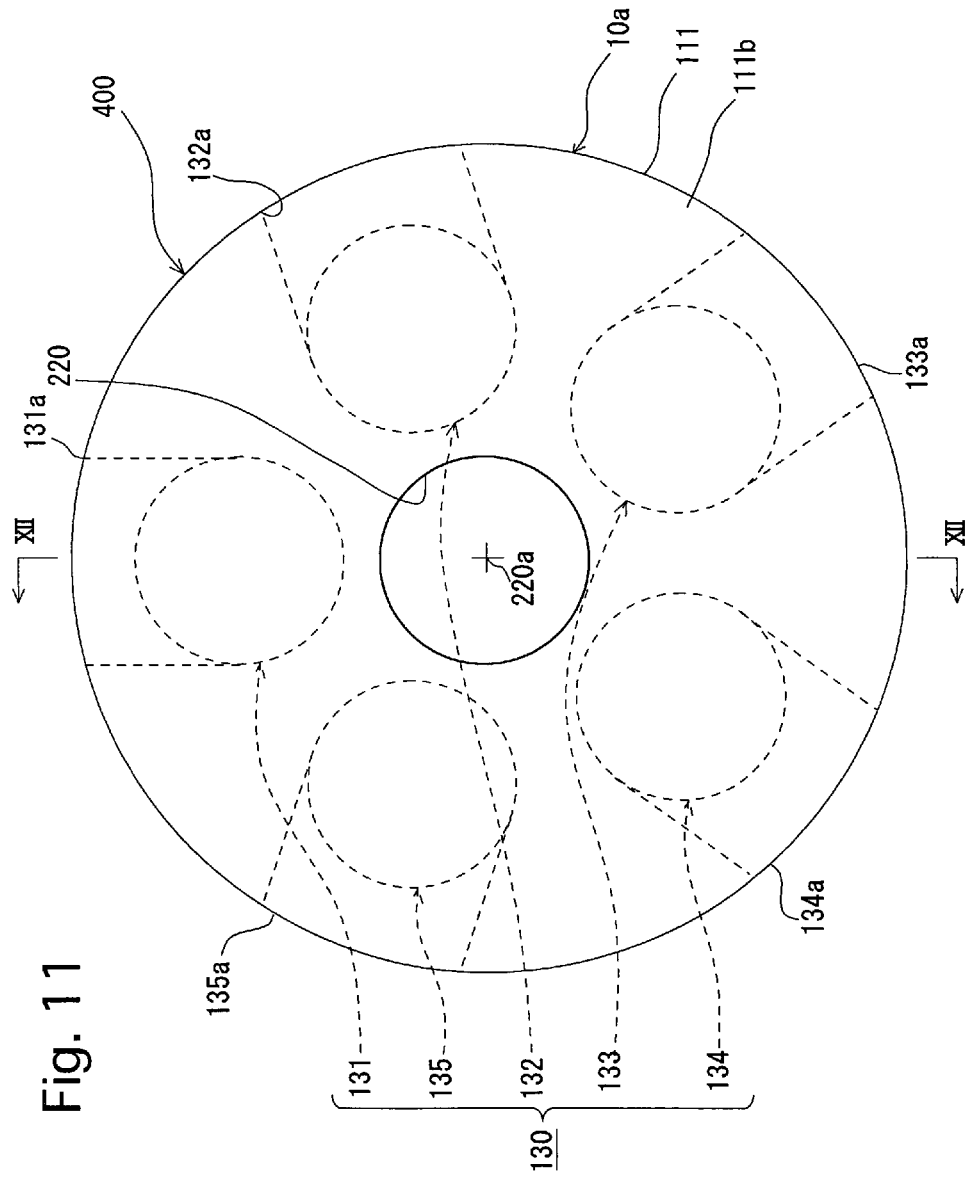
FIG. 11 is a front view showing the configuration of the body of the internal treatment apparatus for a patient, provided with five apertures according to the second embodiment of the present invention.
Figure 12:
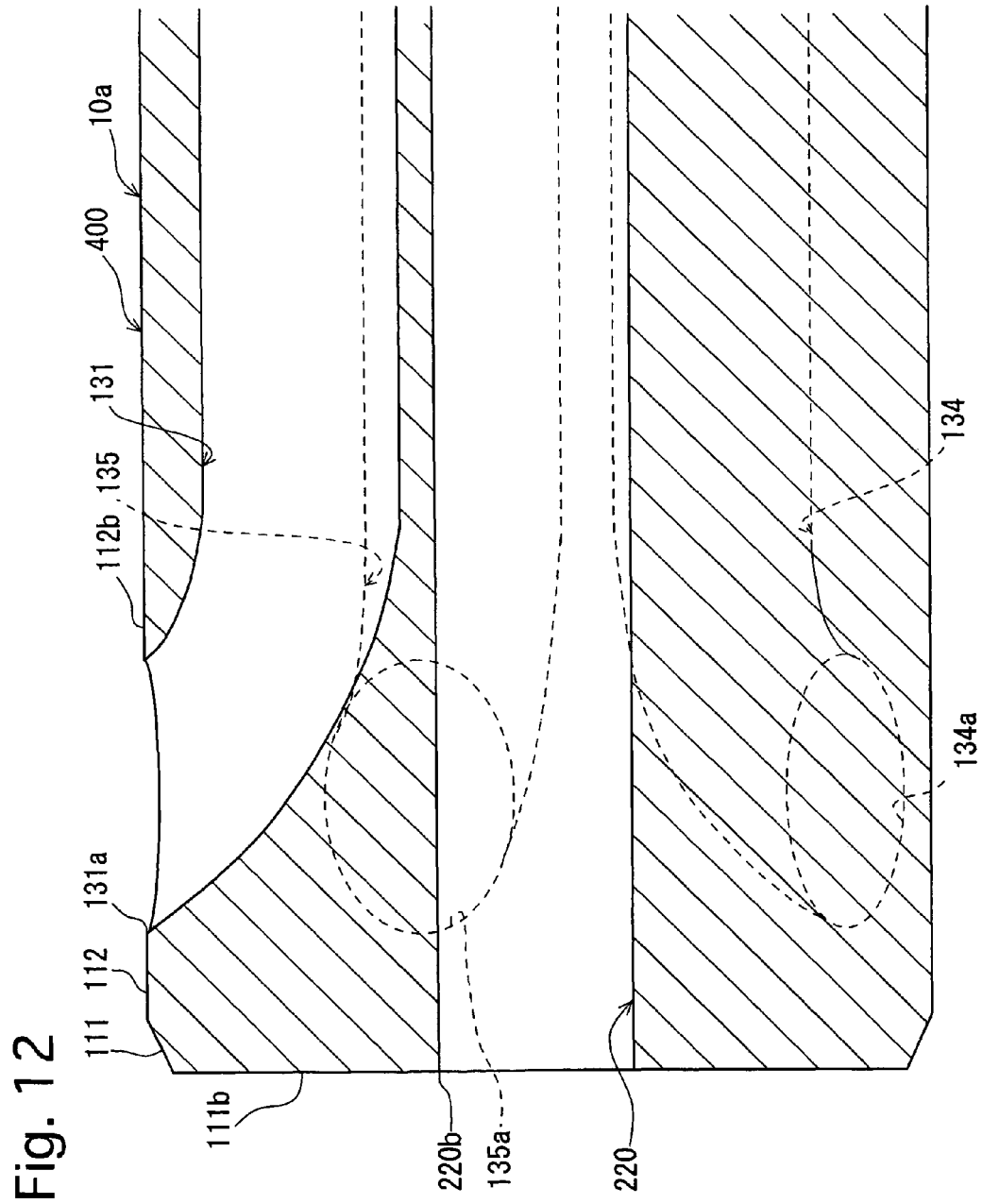
FIG. 12 is a sectional view taken along the line XII-XII of FIG. 11.
Figure 13:
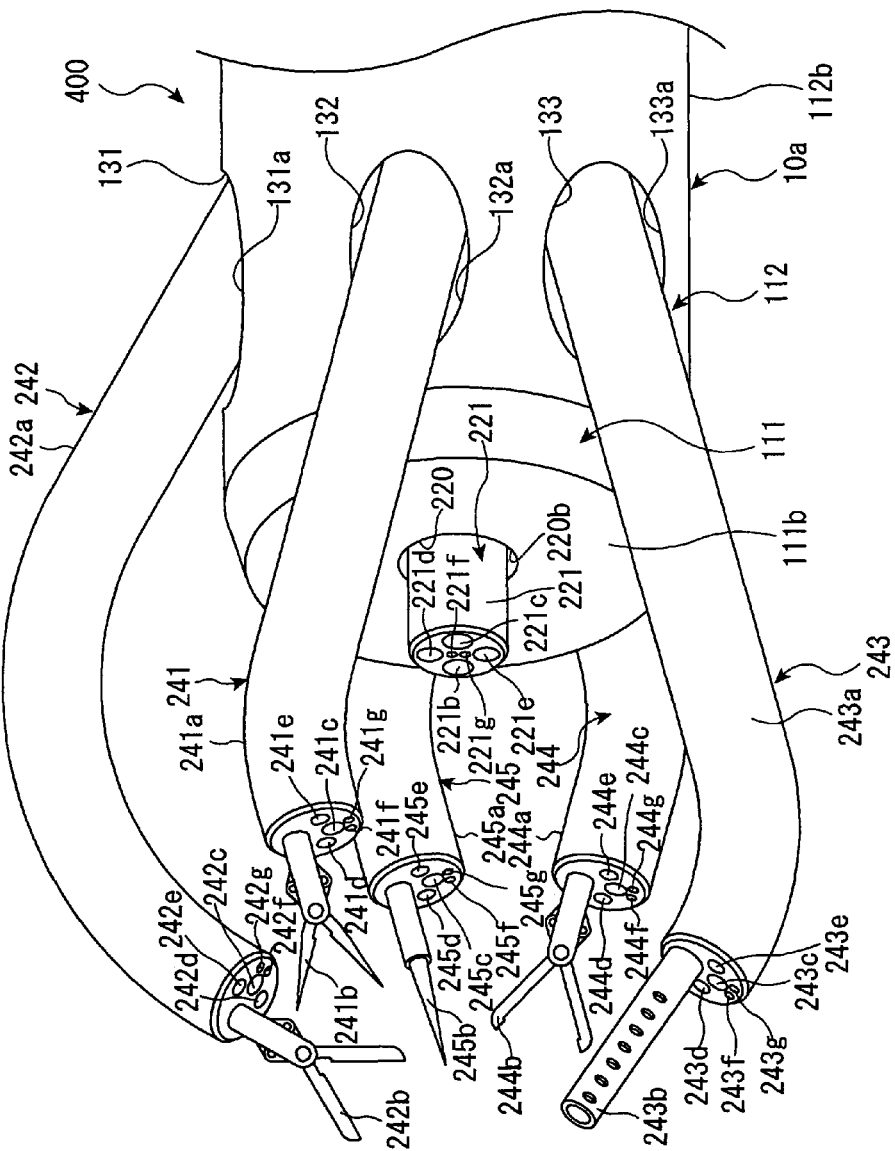
FIG. 13 is a perspective view showing the configuration of the internal treatment apparatus for a patient of FIG. 11 with surgical instruments and an endoscope being inserted therein.

It is possible to employ any number of apertures in the circumferential opening portion 130. For example, as shown in FIGS. 11 to 13, five apertures can be employed in the circumferential opening portion 130. In this example, the circumferential opening portion 130 includes five apertures 131, 132, 133, 134, and 135. The apertures 131, 132, 313, 134, and 135 are disposed at equi-angular intervals (angular intervals of 72 degrees) about a center 220a of the center opening 220 to extend through the apparatus body 10a to reach circular outlets 131a, 132a, 133a, 134a, and 135a provided on the side face 112b, respectively. The outlets 131a, 132a, 133a, 134a, and 135a are disposed at the equal distance from the distal end face 111b. The aforementioned flexible elongated surgical instruments 241, 242, 243, 244, and 245 are retractably inserted into and penetrate the apertures 131, 132, 133, 134, and 135, respectively.

As shown in FIG. 13, the surgical instrument 243 has the following components fixedly inserted into a resiliently deflectable cylindrical body 243a to feed water for cleaning the site of lesion and its surrounding and apply suction to a liquid such as blood or cleaning water at the site of lesion and the surrounding area thereof. The components include a cleaning water feed/suction tube 243b for feeding water to clean the site of lesion and the surrounding area thereof and applying suction to a liquid such as blood or cleaning water at the site of lesion and its surrounding from outside the patient; a monitor optical system (monitor device) 243c for observing the vicinity of the tip of the cleaning water feed/suction tube 243b; illumination optical systems (illumination device) 243d and 243e for illuminating the vicinity of the tip of the cleaning water feed/suction tube 243b with light; and an air feed line 243f (air feed device) for feeding air into the patient and a water feed line 243g (water feed device) for feeding water to the monitor optical system 243c to defog or clean the surface thereof. The surgical instrument 243 is connected at its proximal end portion to surgical instrument manipulating device (not shown) for introducing, withdrawing, and deflecting the body 243a; controlling the feeding of water and applications of suction by the cleaning water feed/suction tube 243b; adjusting the focus, field of view, and zooming of the monitor optical system 243c; adjusting the brightness, direction, and angle of the illumination optical systems 243d and 243e; and feeding water to the monitor optical system 243c to defog or clean the surface thereof and feeding air into the patient. This surgical instrument manipulating device allows the surgical instrument 243 to be operable from outside the patient. The monitor optical system 243c is connected at the proximal end portion of the surgical instrument 243 to image displaying device (not shown) which is capable of displaying the image of the vicinity of the tip of the cleaning water feed/suction tube 243b provided by the monitor optical system 243c. Two monitor optical systems may also be employed to stereoscopically observe the vicinity of the tip of the cleaning water feed/suction tube 243b. It is also possible to make infrared light observations, fluorescent light observations, zoomed observations, ultrasonic observations, confocal observations, or optical coherent tomographic(OCT) observations.

As shown in FIG. 13, the surgical instrument 244 has the following components fixedly inserted into a resiliently deflectable cylindrical body 244a to locally stop bleeding at a desired portion. The components include an RF hemostatic forceps 244b for applying a radio frequency locally to a desired portion and thereby generating heat to stop bleeding; a monitor optical system (monitor device) 244c for observing the vicinity of the tips of the RF hemostatic forceps 244b; illumination optical systems (illumination device) 244d and 244e for illuminating the vicinity of the tips of the RF hemostatic forceps 244b with light; and an air feed line 244f (air feed device) for feeding air into the patient and a water feed line 244g (water feed device) for feeding water to the monitor optical system 244c to defog or clean the surface thereof. The surgical instrument 244 is connected at its proximal end portion to surgical instrument manipulating device (not shown) for introducing, withdrawing, and deflecting the body 244a; controlling the hemostatic operations provided by the RF hemostatic forceps 244b; adjusting the focus, field of view, and zooming of the monitor optical system 244c; adjusting the brightness, direction, and angle of the illumination optical systems 244d and 244e; and feeding water to the monitor optical system 244c to defog or clean the surface thereof and feeding air into the patient. This surgical instrument manipulating device allows the surgical instrument 244 to be operable from outside the patient. The monitor optical system 244c is connected at the proximal end portion of the surgical instrument 244 to image displaying device (not shown) which is capable of displaying the image of the vicinity of the tips of the RF hemostatic forceps 244b provided by the monitor optical system 244c. Two monitor optical systems may also be employed to stereoscopically observe the vicinity of the tips of the RF hemostatic forceps 244b. It is also possible to make infrared light observations, fluorescent light observations, zoomed observations, ultrasonic observations, confocal observations, or optical coherent tomographic (OCT) observations.

As shown in FIG. 13, the surgical instrument 245 has the following components fixedly inserted into a resiliently deflectable cylindrical body 245a to incise a desired portion. The components include an RF incision knife 245b for pushing its RF-vibrating tip portion against a desired portion for incision; a monitor optical system (monitor device) 245c for observing the vicinity of the tip of the RF incision knife 245b; illumination optical systems (illumination device) 245d and 245e for illuminating the vicinity of the tip of the RF incision knife 245b with light; and an air feed line 245f (air feed device) for feeding air into the patient and a water feed line 245g (water feed device) for feeding water to the monitor optical system 245c to defog or clean the surface thereof. The surgical instrument 245 is connected at its proximal end portion to surgical instrument manipulating device (not shown) for introducing, withdrawing, and deflecting the body 245a; controlling the incision operations provided by the RF incision knife 245b; adjusting the focus, field of view, and zooming of the monitor optical system 245c; adjusting the brightness, direction, and angle of the illumination optical systems 245d and 245e; and feeding water to the monitor optical system 245c to defog or clean the surface thereof and feeding air into the patient. This surgical instrument manipulating device allows the surgical instrument 245 to be operable from outside the patient. The monitor optical system 245c is connected at the proximal end portion of the surgical instrument 245 to image displaying device (not shown) which is capable of displaying the image of the vicinity of the tip of the RF incision knife 245b provided by the monitor optical system 245c. Two monitor optical systems may also be employed to stereoscopically observe the vicinity of the tip of the RF incision knife 245b. It is also possible to make infrared light observations, fluorescent light observations, zoomed observations, ultrasonic observations, confocal observations, or optical coherent tomographic (OCT) observations.

The surgical instruments 241, 242, 243, 244, and 245 being preferably equal in outer diameter could be inserted into any aperture according to the contents and steps of the surgical procedure. It is also desirable to make the inner diameter of the outlets 131a, 132a, 133a, 134a, and 135a greater than the outer diameter of the surgical instruments 241, 242, 243, 244, and 245 to use the surgical instruments 241, 242, 243, 244, and 245 at desired angles.

Figure 7:
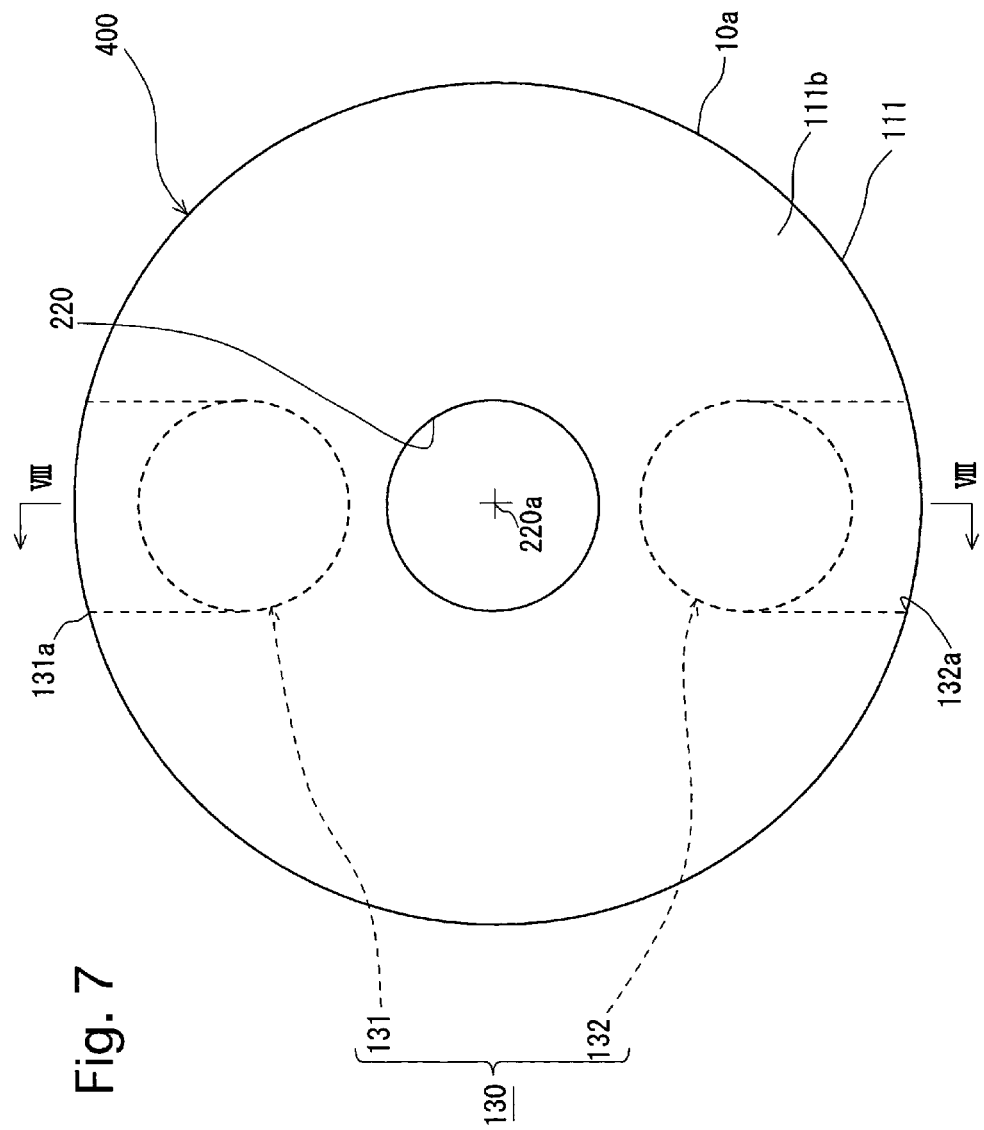
FIG. 7 is a front view showing the configuration of the body of an internal treatment apparatus for a patient according to a second embodiment of the present invention.
Figure 8:
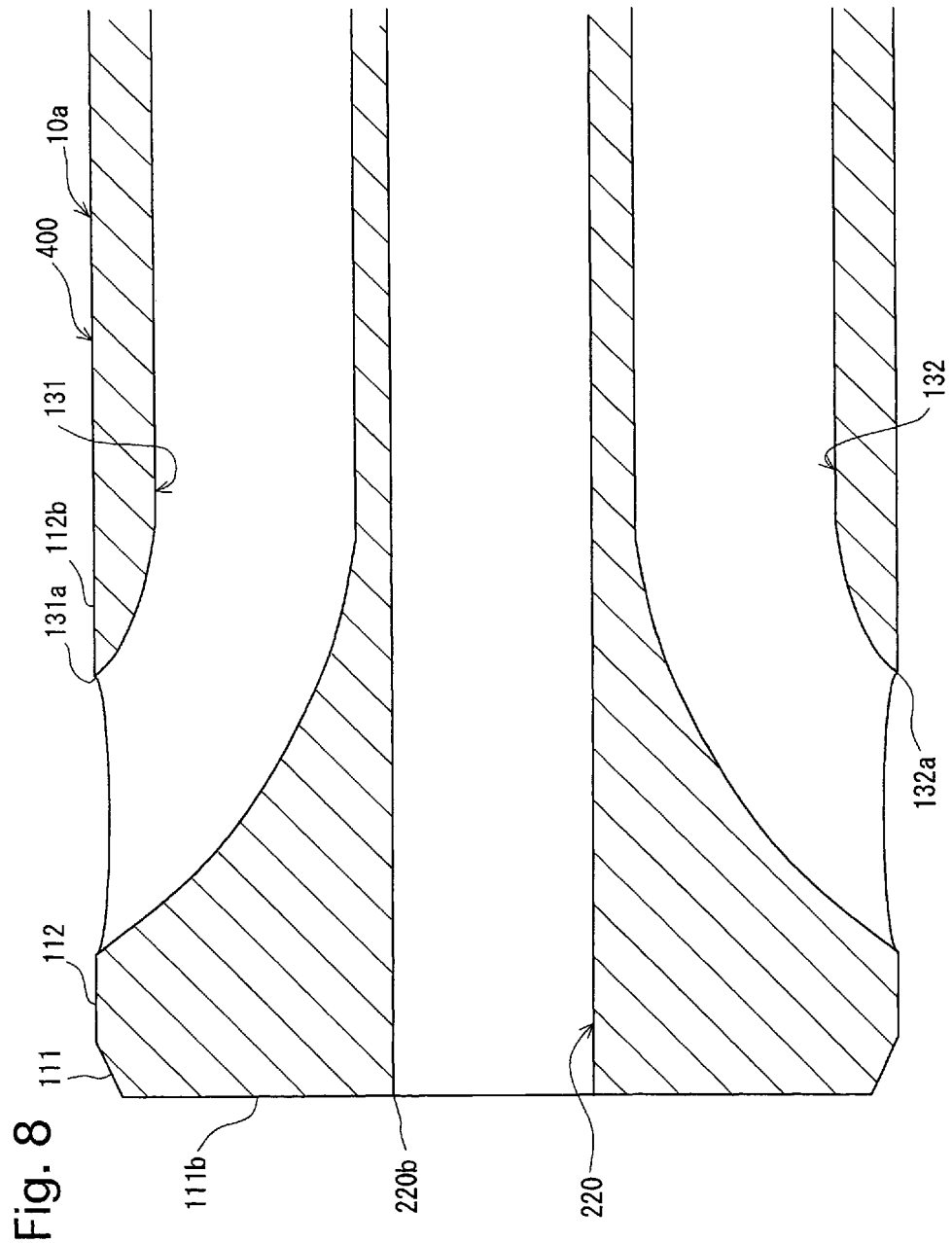
FIG. 8 is a sectional view taken along the line VIII-VIII of FIG. 7.

The following is an explanation on a surgical procedure performed on a site of lesion using the internal treatment apparatus 400 and the internal treatment system 500, shown in FIGS. 7 through 9. First, an adequate portion is incised to perform a surgical procedure on a site of lesion in a patient. Even for a surgical procedure that requires a plurality of surgical instruments, the internal treatment apparatus 400 would require an incised portion just large enough to introduce therethrough the internal treatment apparatus 400 into the patient (e.g., about 5 cm for the apparatus body 10a having an outer diameter of 5 cm), thereby reducing the burden on the patient.

Thereafter, as shown in FIG. 14, the internal treatment apparatus 400 is introduced into a patient 50 through the incised portion. Before the insertion, the body manipulating device 260, the endoscope manipulating device 170, the surgical instrument manipulating devices 181 and 182, and the image displaying device 187 and 191 have been already connected to the apparatus body 10a, the stereoscopic endoscope 221, and the surgical instruments 241 and 242 in the internal treatment apparatus 400. When introduced into the patient 50, the surgical instruments 241 and 242 are preferably accommodated inside the apparatus body 10a without being protruded from the outlets 131a and 132a by manipulating the surgical instrument manipulating devices 181 and 182. This is to prevent the surgical instruments 241 and 242 from being protruded from the apparatus body 10a to hurt the patient 50 during the introduction. The internal treatment apparatus 400 is introduced into the patient and then stopped to start the surgical procedure when a view range 22 of the stereoscopic endoscope 221 allows the operator to view a lesion 55 and the surrounding area thereof and each tip portion of the surgical instruments 241, 242, as shown in FIG. 10.

The internal treatment apparatus 400 is designed such that the surgical instruments 241 and 242 are arranged to surround the stereoscopic endoscope 221, thereby allowing the surgical instruments 241 and 242 to come into the view provided by the stereoscopic endoscope 221 from its periphery during the surgical procedure. This allows the operator to easily recognize the lesion 55 and the surgical instruments 241 and 242, thereby facilitating the manipulation thereof. Furthermore, the stereoscopic endoscope 221 is protruded from the distal end face 111b while the surgical instruments 241 and 242 are protruded from the side face 112b, thereby reducing the risk of the surgical instruments 241 and 242 being interfered with each other. Accordingly, for a lesion 55 located deep inside the patient, the internal treatment apparatus 400 can be introduced deep into the patient, thereby performing the surgical procedure smoothly and with safety. The following are explanations of modifications of the second embodiment, according to the present invention.

The illumination light which is emitted from the illumination optical systems 221d and 221e can be white light, and the illumination light which is emitted from each of the illumination optical systems 241d, 241e, 242d, 242e, 243d, 243e, 244d, 244e, 245d and 245e can be colored light. According to this arrangement, if the surgical instruments 241 through 245 are directed toward the center axis 10b of the apparatus body 10a, colored light appears within the field-of-view of the stereoscopic endoscope 221, and the farther the surgical instruments 241 through 245 are moved away from the center axis 10b, the amount of colored light which appears within the field-of-view of the stereoscopic endoscope 221 decreases. If such a characteristic is utilized, operation of the surgical instruments 241 through 245 is facilitated because the bending direction of the surgical instruments 241 through 245 can be visually confirmed. It is desirable for the illumination light emitted from the illumination optical systems 221d, 221e, 241d, 241e, 242d, 242e, 243d, 243e, 244d, 244e, 245d and 245e, to be changeable between white light and colored light.

Furthermore, it is desirable for each colored light emitted from the surgical instruments 241 through 245 to be set so as to have a different wavelength from each other. Accordingly, the bending direction of each of the surgical instruments 241 through 245 can be visually confirmed individually. The white light and colored light can be continuous light or intermitting light, and if a combination of continuous light and intermitting light is applied, light emitted from the illumination optical systems 221d and 221e and light emitted from the illumination optical systems 221d, 221e, 241d, 241e, 242d, 242e, 243d, 243e, 244d, 244e, 245d and 245e can be easily distinguished visually. Furthermore, if the wavelength of the colored light is altered in accordance with time, by changing the colored illumination state within the field-of-view of the stereoscopic endoscope 221 during an operation, an object under observation can be easily confirmed visually in the case where one illumination color is insufficient for observation throughout the duration of an operation.

Furthermore, the intensity of light emitted from the illumination optical systems 221d and 221e can be made to differ from the intensity of light emitted from the illumination optical systems 221d, 221e, 241d, 241e, 242d, 242e, 243d, 243e, 244d, 244e, 245d and 245e. Accordingly, since the light emitted from the illumination optical systems 221d and 221e, and the light emitted from the illumination optical systems 221d, 221e, 241d, 241e, 242d, 242e, 243d, 243e, 244d, 244e, 245d and 245e can be easily distinguished, the bending directions of the surgical instruments 241 through 245 can be visually confirmed, facilitating the operation thereof.

Figure 15:
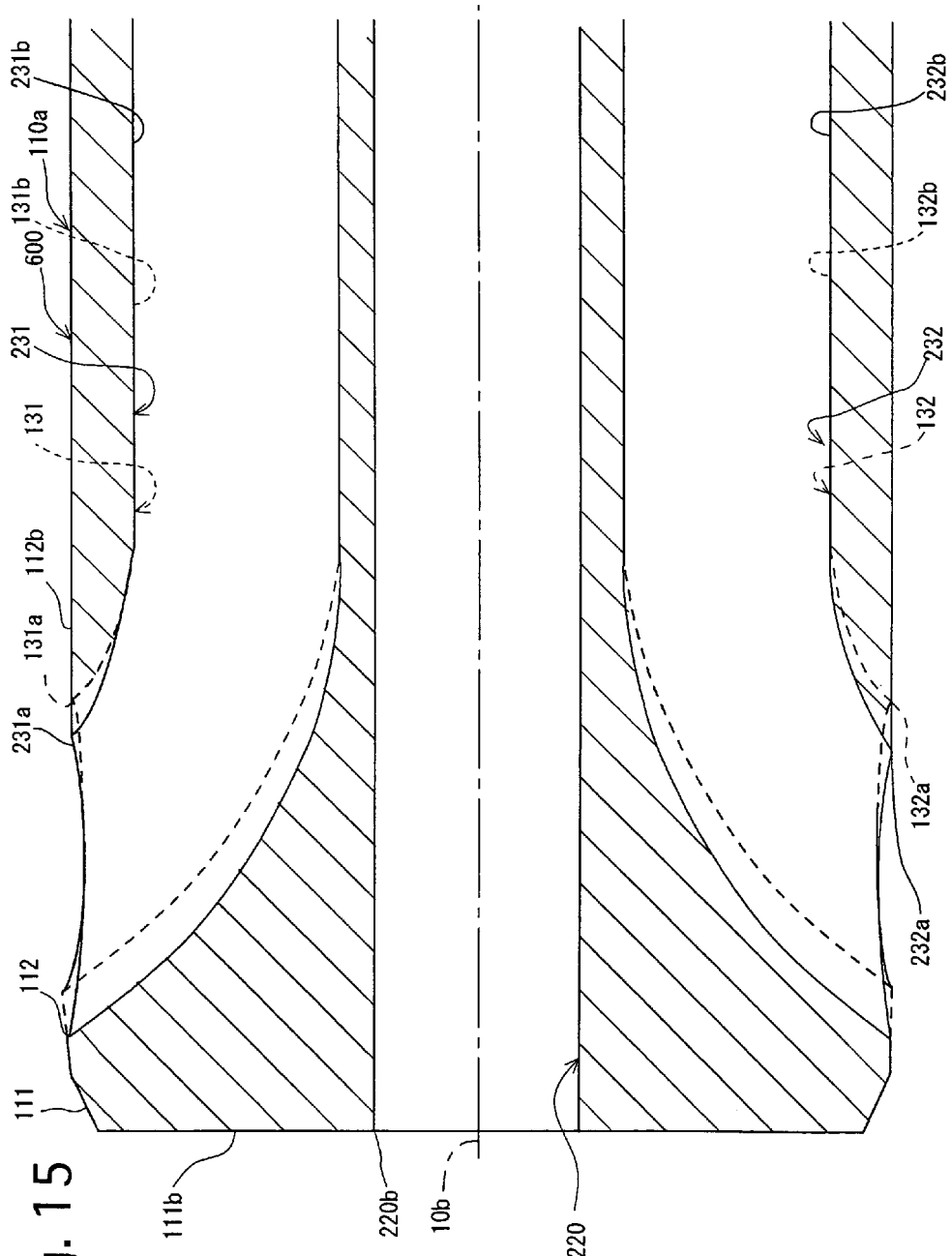
FIG. 15 shows a modification of the second embodiment, of the present invention, and corresponds to FIG. 8.

As shown in FIG. 15, instead of the two circular apertures 131 and 132, two circular apertures 231 and 232 are provided. Two channels 231b and 232b of the two circular apertures 231 and 232 extend parallel to a center axis 10b of an apparatus body 110a, and are the same as two channels 131b and 132b, of the two circular apertures 131 and 132, which extend parallel to the center axis 10b of the apparatus body 10a. Outlets 231a and 232a are provided closer to than the bottom face (distal end face) 111b than the outlets 131a and 132a. Accordingly, compared to the two circular apertures 131 and 132, the angle by which surgical instruments 341 and 342 (see FIG. 16) project out of the two circular apertures 231 and 232 of the apparatus body 110a (i.e., the angle with respect to the center axis 10b of the apparatus body 110a) is smaller.

Figure 16:
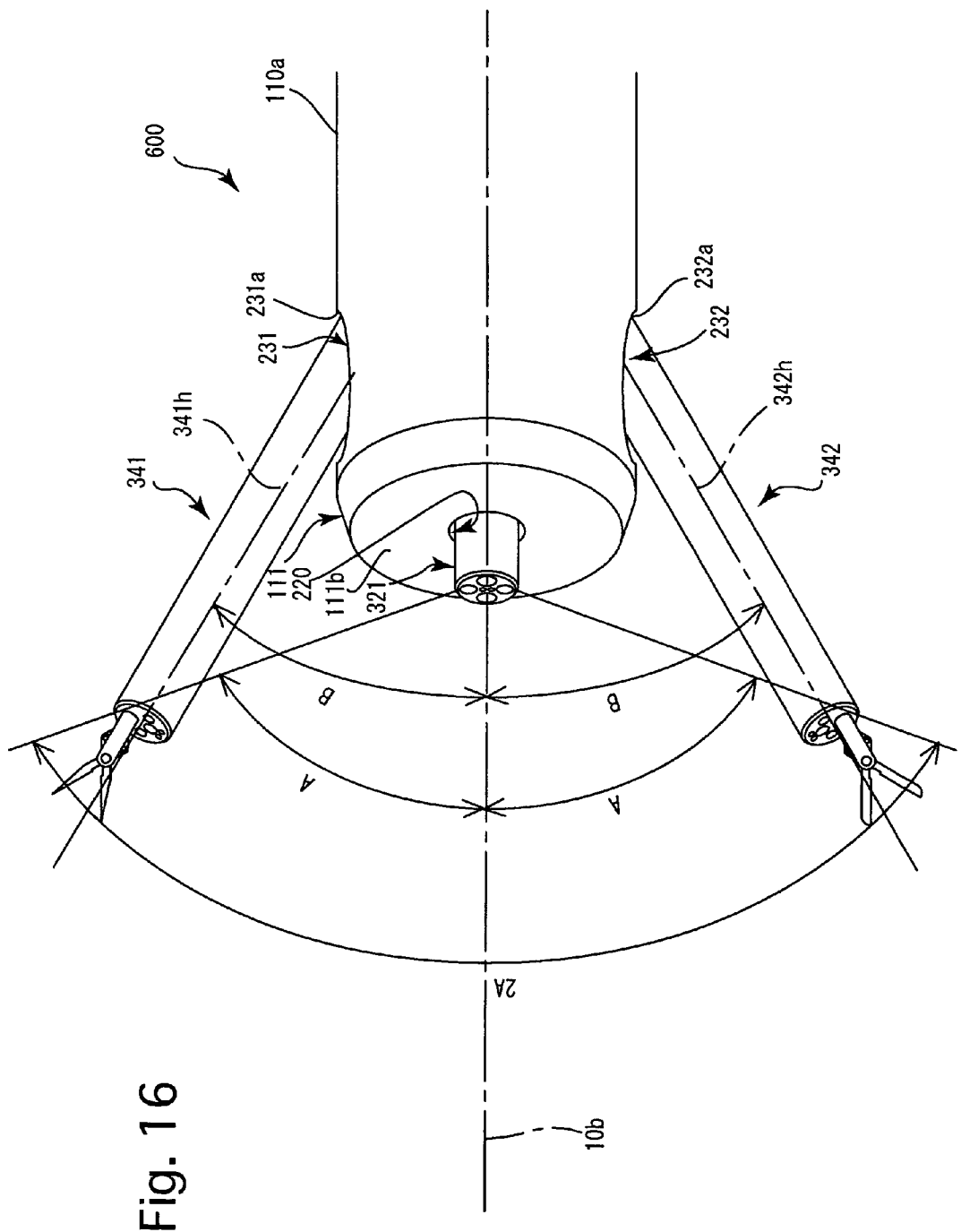
FIG. 16 is a perspective view showing the configuration of the internal treatment apparatus with surgical instruments and an endoscope being inserted therein in the modified second embodiment shown in FIG. 15.

FIG. 16 shows the internal treatment apparatus 600 with surgical instruments 341 and 342 being inserted into apertures 231 and 232, respectively, in the modified second embodiment of FIG. 15. The angle by which the surgical instrument 341 projects out of the apparatus body 110a from the outlet 231a (i.e., the angle between the center axis 10b and the surgical instrument 341 when extended in a straight line (center axis 341h)), and the angle by which the surgical instrument 342 projects out of the apparatus body 110a from the outlet 232a (i.e., the angle between the center axis 10b and the surgical instrument 342 when extended in a straight line (center axis 342h)), are represented as 'B' in FIG. 16, and the total angle '2B' thereof is less than the field-of-view 2A of the stereoscopic endoscope 321. According to this construction, the distal ends of the surgical instruments 341 and 342 can easily fit into the field-of-view of the stereoscopic endoscope 321 even if the surgical instruments 341 and 342 are projected outwards in a straight line, so that a safe and reliable treatment operation can be carried out quickly and easily. Note that so long as the projection angle of each of the surgical instruments 341 and 342 is smaller than 'A', i.e., the half-angle of the field-of-view of the stereoscopic endoscope 321, the angle of each of the surgical instruments 341 and 342 can be set to a desired angle. Furthermore, it is desirable for the distal end portions of the surgical instruments 341 and 342 to be semi-hard rather than flexible in order to maintain the projection angle thereof.

Figure 17:
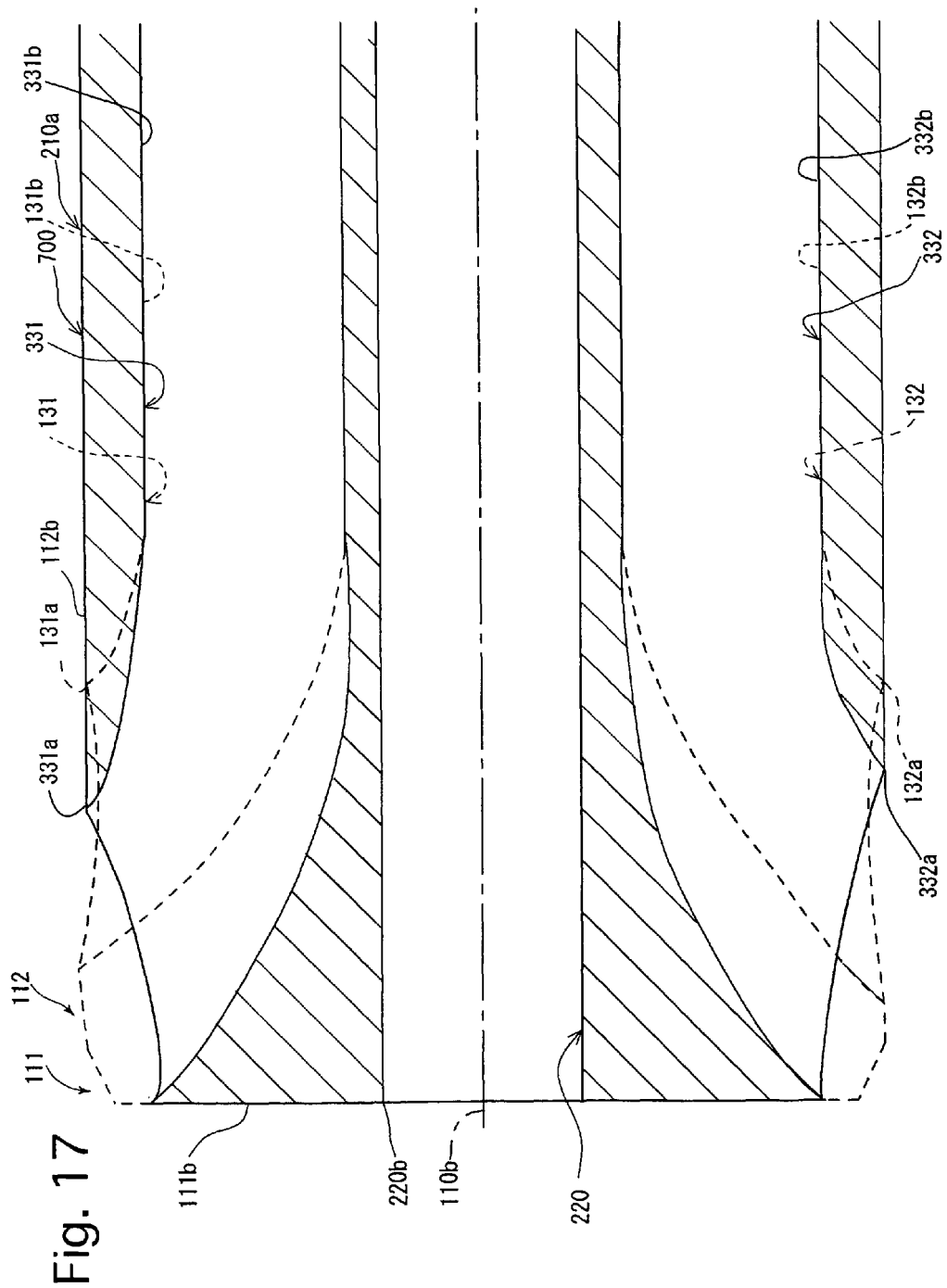
FIG. 17 shows another modification of the second embodiment of the present invention, corresponding to FIG. 8.

As shown in FIG. 17, instead of the two circular apertures 131 and 132, two circular apertures 331 and 332 are provided. Two channels 331b and 332b of the two circular apertures 331 and 332 extend parallel to a center axis 110b of an apparatus body 210a, and are the same as two channels 131b and 132b, of the two circular apertures 131 and 132, which extend parallel to the center axis 10b of the apparatus body 10a. Outlets 331a and 332a are provided so as to extend over the resiliently deflectable portion 112 and the bottom face (distal end face) 111b. Accordingly, compared to the two circular apertures 131 and 132, the angle by which surgical instruments 441 and 442 (see FIG. 18) project out of the two circular apertures 331 and 332 of the apparatus body 210a (i.e., the angle with respect to the center axis 110b of the apparatus body 210a) is smaller.

Figure 18:
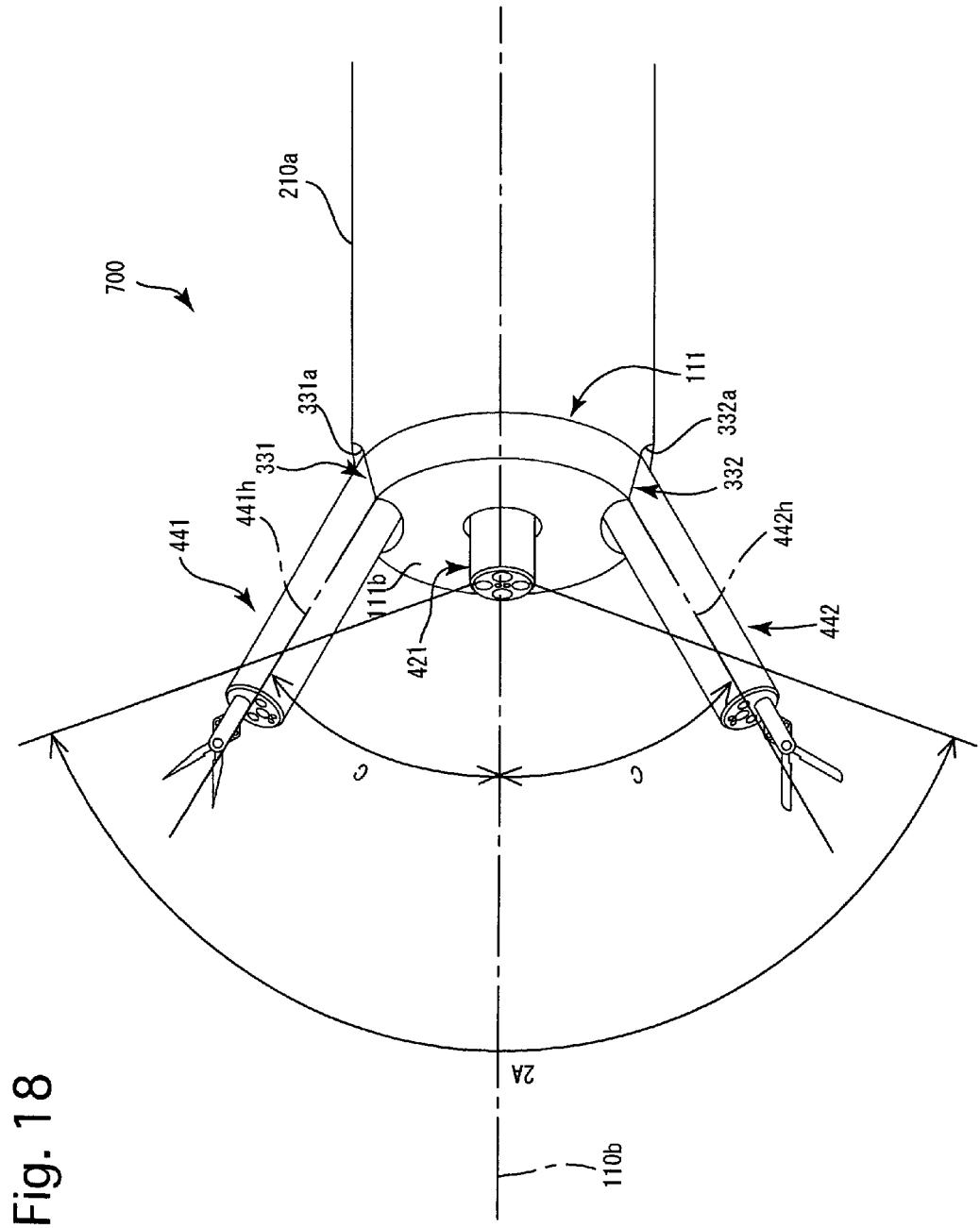
FIG. 18 is a perspective view showing the configuration of the internal treatment apparatus with surgical instruments and an endoscope being inserted therein in the modified second embodiment shown in FIG. 17.

FIG. 18 shows the internal treatment apparatus 700 with surgical instruments 441 and 442 being inserted into apertures 331 and 332, respectively, in the modified second embodiment of FIG. 17. The angle by which the surgical instrument 441 projects out of the apparatus body 210a from the outlet 331a (i.e., the angle between the center axis 110b and the surgical instrument 441 when extended in a straight line (center axis 441h)), and the angle by which the surgical instrument 442 projects out of the apparatus body 210a from the outlet 332a (i.e., the angle between the center axis 110b and the surgical instrument 442 when extended in a straight line (center axis 442h)), are represented as 'C' in FIG. 18, and the total angle '2C' thereof is less than the field-of-view 2A of the stereoscopic endoscope 421. According to this construction, the distal ends of the surgical instruments 441 and 442 can easily fit into the field-of-view of the stereoscopic endoscope 421 even if the surgical instruments 441 and 442 are projected outwards in a straight line, so that a safe and reliable treatment operation can be carried out quickly and easily. Note that so long as the projection angle of each of the surgical instruments 441 and 442 is smaller than 'A', i.e., the half-angle of the field-of-view of the stereoscopic endoscope 421, the angle of each of the surgical instruments 441 and 442 can be set to a desired angle. Furthermore, it is desirable for the distal end portions of the surgical instruments 441 and 442 to be semi-hard rather than flexible in order to maintain the projection angle thereof.

Figure 19:
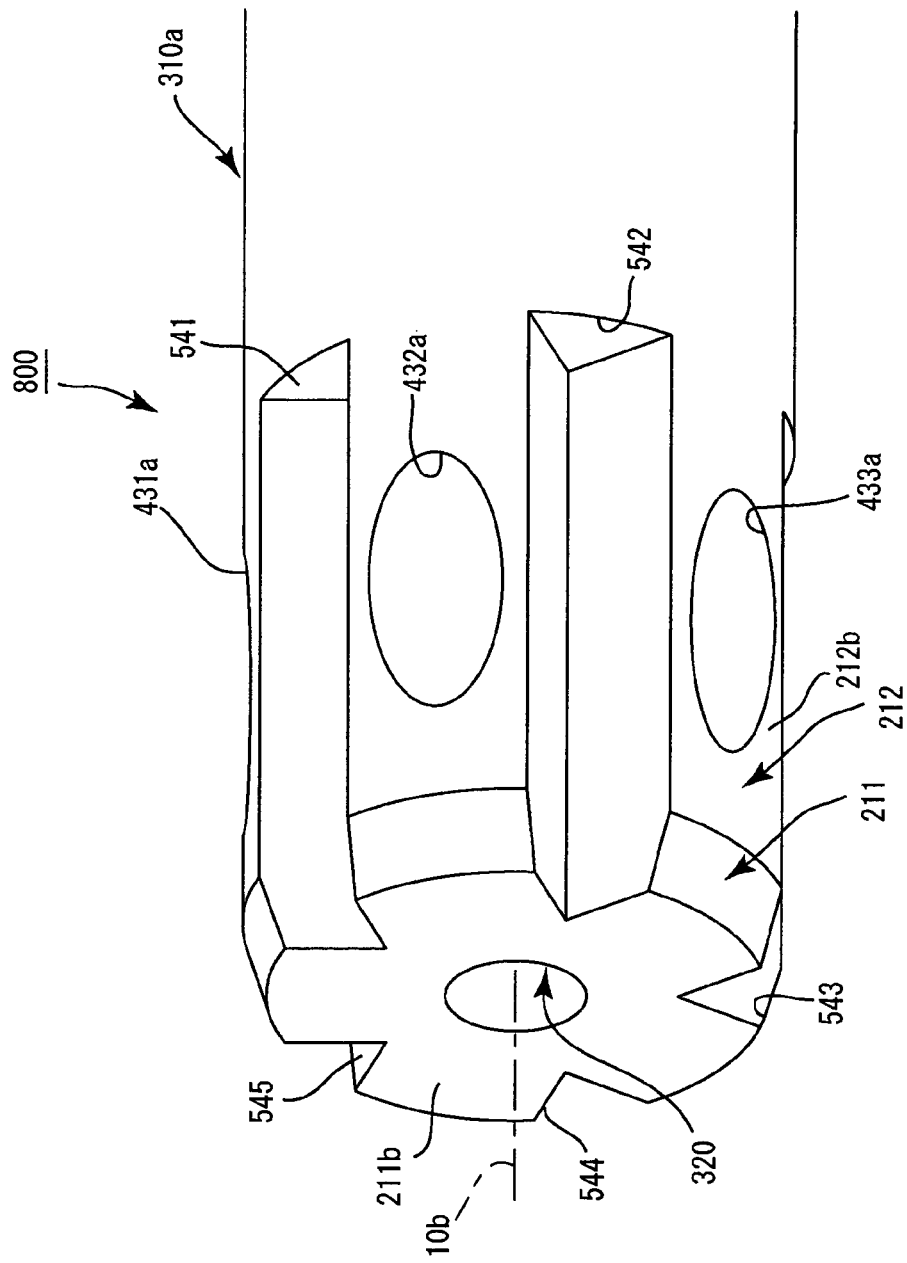
FIG. 19 shows another modification of the second embodiment of the present invention.

As shown in FIG. 19, grooves 541 through 545 having the same shape and concaved in a direction from the side face 212b to the 10b can be provided in each space between two adjacent outlets 431a and 435a (outlets 434a and 435a are not shown in FIG. 19) provided on the side face 212b at equiangular intervals around the center opening 320. According to this construction, since the amount of surface area to which the distal end portion 211 and the resiliently deflectable portion 212 touches internal tissue of the patient 50 can be reduced, it becomes easier to insert the internal treatment apparatus 800 into the patient 50, and hence reducing the burden on both the patient and the operator (practitioner). The grooves 541 through 545 can be of a desired shape so long as the amount of surface area to which the distal end portion 211 and the resiliently deflectable portion 212 touches internal tissue of the patient 50 can be reduced.

Other configurations, operations, effects, and modified examples such as those of the first embodiment can also be applied to the second embodiment.

According to an aspect of the present invention, surgical instruments can be placed at equal angular intervals around an endoscope for observing a target site. This reduces the length of an incised portion for surgical procedures performed on a site of lesion inside a patient even when a plurality of surgical instruments are introduced at the same time through the incised portion. Additionally, for a surgical procedure performed on a site of lesion located deep inside the patient, it is possible to ensure an adequate view range without increasing the length of the incised portion. Furthermore, the surgical instruments are placed so as to surround the endoscope for observing the site of lesion, thereby preventing the surgical instruments from interfering with each other and obstructing the view, and allowing the operator to perform the surgical procedure smoothly.

According to another aspect of the present invention, an endoscope is protruded from a bottom face of the cylindrical body while surgical instruments are protruded from the side face. This configuration prevents the surgical instruments from obstructing the view window of the endoscope and restricting the field of view, thereby eliminating the difficulty of viewing the site of lesion and the surrounding area thereof. Furthermore, a plurality of surgical instruments could be introduced into the patient to access the site of lesion from the periphery of the view range provided by the endoscope. This reduces the risk of interference between the surgical instruments or the surgical instruments and the endoscope, thus allowing the surgical instruments and the endoscope to positively access the site of lesion. This also allows the surgical instruments and the endoscope accommodated inside the body to be introduced into the patient, thereby reducing the length of an incised portion even when a plurality of surgical instruments are introduced at the same time through the incised portion.

Obvious changes may be made in the specific embodiments of the present invention described herein, such modifications being within the spirit and scope of the invention claimed. It is indicated that all matter contained herein is illustrative and does not limit the scope of the present invention.

Industrial Applicability

According to the present invention, the internal treatment apparatus is designed such that the surgical instruments are arranged to surround the stereoscopic endoscope, thereby allowing the surgical instruments to be placed along the entire circumference of a view range provided by the stereoscopic endoscope during the surgical procedure. This allows the operator to easily recognize the lesion and the surgical instruments, thereby facilitating the manipulation thereof. Additionally, the surgical instruments can be replaced as appropriate to facilitate a surgical operation. Furthermore, for a lesion located deep inside the patient, the internal treatment apparatus can be introduced deep into the patient to provide a view range, thereby allowing the surgical procedure to be performed smoothly with safety.

The invention claimed is:

1. An internal treatment apparatus for a patient comprising a flexible tubular body to be introduced into a patient, said flexible tubular body comprising:
   a center opening and an endoscope inserted through said center opening for observing a target site, said center opening extending through said flexible tubular body from a center of a flat distal end face of said flexible tubular body, said flat distal end face facing said target site, said center opening having an outlet with an outlet perimeter lying in a common plane with said flat distal end face,
   a distal end portion having a circular cross section with the outer diameter thereof reduced toward its distal end to said flat distal end face, and
   a plurality of circumferential holes through which surgical instruments are inserted for performing a surgical procedure on said target site, each of said plurality of circumferential holes being provided proximally of said distal end portion having a reduced diameter and extending through a side face of said flexible tubular body so that each of said plurality of circumferential holes is independent from said flat distal end face, and each of said plurality of circumferential holes is distinct from said center opening.

2. The internal treatment apparatus for a patient according to claim 1, wherein said flexible tubular body comprises a resiliently deflectable portion, and a circumferential opening portion includes said plurality of circumferential holes, and the circumferential opening portion passes through said flexible tubular body from a side face of the deflectable portion toward a proximal end face of said flexible tubular body.

3. An internal treatment system for a patient comprising:
   a flexible tubular body to be introduced into a patient, said flexible tubular body including a center opening and an endoscope inserted through said center opening for observing a target site, said center opening being circular in cross section and extending through said flexible tubular body from a center of a flat distal end face of said flexible tubular body, said distal end face facing said target site, said center opening having an outlet with an outlet perimeter lying in a common plane with said flat distal end face, a distal end portion having a circular cross section with the outer diameter thereof reduced toward its distal end to said flat distal end face, and a plurality of circumferential holes through which surgical instruments are inserted for performing a surgical procedure on said target site, each of said plurality of circumferential holes being provided proximally of said distal end portion having a reduced diameter and extending through a side face of said flexible tubular body at a distal end of said flexible tubular body, so that each of said plurality of circumferential holes is independent from said flat distal end face, and each of said plurality of circumferential holes is distinct from said center opening;
   a body manipulating device for manipulating said flexible tubular body from outside said patient;
   an endoscope manipulating device for manipulating said endoscope from outside said patient; and
   a surgical instrument manipulating device for manipulating said surgical instruments from outside said patient.

4. The internal treatment system for a patient according to claim 3, wherein said flexible tubular body comprises a resiliently deflectable portion, and a circumferential opening portion includes said plurality of circumferential holes, and the circumferential opening portion passes through said flexible tubular body from a side face of the deflectable portion toward a proximal end face of said flexible tubular body.

* * * * *